US009694045B2

(12) United States Patent
Lee et al.

(10) Patent No.: US 9,694,045 B2
(45) Date of Patent: Jul. 4, 2017

(54) PHARMACEUTICAL COMPOSITION FOR PREVENTING OR TREATING INFLAMMATORY DISEASES COMPRISING TRACHELOSPERMI CAULIS EXTRACT AND PAEONIA SUFFRUTICOSA ANDREWS EXTRACT, AND METHOD FOR PREPARING THE SAME

(75) Inventors: Jeong Min Lee, Gunpo-si (KR); Jae Won Park, Seoul (KR); Jung Ho Choi, Daejeon (KR); Ill Chan Noh, Icheon-si (KR); Se Na Kim, Eumseong-gun (KR); Young June Lee, Busan (KR); Kyu Seok Choi, Daejeon (KR); Ji Na Choi, Daejeon (KR); Whan Soo Choi, Seoul (KR); Jin Tea Hong, Cheongju-si (KR)

(73) Assignee: SINIL PHARMACEUTICAL CO., LTD., Chungju-si (KR)

(*) Notice: Subject to any disclaimer, the term of this patent is extended or adjusted under 35 U.S.C. 154(b) by 64 days.

(21) Appl. No.: 13/991,418

(22) PCT Filed: Aug. 18, 2011

(86) PCT No.: PCT/KR2011/006094
§ 371 (c)(1),
(2), (4) Date: Aug. 19, 2013

(87) PCT Pub. No.: WO2012/074183
PCT Pub. Date: Jun. 7, 2012

(65) Prior Publication Data
US 2014/0010899 A1 Jan. 9, 2014

(30) Foreign Application Priority Data

Dec. 3, 2010 (KR) .................. 10-2010-0123086
Jul. 20, 2011 (KR) .................. 10-2011-0072011
Jul. 20, 2011 (KR) .................. 10-2011-0072020

(51) Int. Cl.
A61K 36/24 (2006.01)
A61K 36/65 (2006.01)
A61K 9/20 (2006.01)
A23L 33/105 (2016.01)

(52) U.S. Cl.
CPC ............ *A61K 36/65* (2013.01); *A23L 33/105* (2016.08); *A61K 9/2009* (2013.01); *A61K 9/2054* (2013.01); *A61K 9/2081* (2013.01); *A61K 36/24* (2013.01)

(58) Field of Classification Search
CPC .............................. A61K 36/24; A61K 36/65
See application file for complete search history.

(56) References Cited

U.S. PATENT DOCUMENTS 8,455,014 B2 * 6/2013 Lee et al. ............ 424/725
2009/0285913 A1 * 11/2009 Lee et al. ............ 424/725
2009/0317495 A1 * 12/2009 Lee et al. ............ 424/725

FOREIGN PATENT DOCUMENTS

| AU | 2009101063 A4 | 2/2010 |
|---|---|---|
| CN | 1207908 A | 2/1999 |
| CN | 1788753 A | 6/2006 |
| CN | 101085728 A | 12/2007 |
| GB | 2463080 A | 3/2010 |
| JP | 61-106515 A | 5/1986 |
| JP | 2002-241266 A | 8/2002 |
| JP | 2010-516755 A | 5/2010 |
| KR | 10-2008-0035219 A | 4/2008 |
| KR | 100847440 B1 * | 7/2008 |
| KR | 10-2011-0034158 A | 4/2011 |
| WO | 2008/004804 A1 | 1/2008 |

(Continued)

OTHER PUBLICATIONS

Lee et al. (2007) J. Pharmacy and Pharmacology, 59: 123-130.*
Oh et al. (2003) J. Ethnopharmacology 84: 85-89.*
Hong et al. (2010) Biosci. Biotechnol. Biochem., 74(6), 1152-1156.*
Zhang et al. (2012) International Immunopharmacology 14, 27-31.*
Wu et al. (Advance Access Publication Jun. 15, 2007) eCAM 2009: 6(1): 57-63.*
Oh et al. (2004) International Immunopharmacology 4: 377-386.*
Khanna et al. (2007) Current Opinion in Pharmacology 7: 344-351.*

(Continued)

*Primary Examiner* — Chris R Tate
*Assistant Examiner* — Russell Fiebig
(74) *Attorney, Agent, or Firm* — Cooley LLP

(57) ABSTRACT

The present invention relates to a pharmaceutical composition for preventing and treating an inflammatory disease, including a mixture of extracts from *Trachelospermi Caulis* and *Paeonia Suffruticosa* Andrews as an active ingredient and method for preparing the same. Also, a quasi-drug composition, a health functional food composition and a cosmetic composition, all based on the mixture, are provided for preventing or improving inflammation. In addition, the present invention relates to a method for treating an inflammatory disease by administering the pharmaceutical composition to a subject suspected of having the inflammatory disease. Containing the extract mixture, the composition exhibits excellent anti-inflammatory activity and edema-suppressing activity, compared to individual extracts, and thus can be applied to the prevention, treatment or improvement of an inflammatory disease. As natural materials, the extracts can be used as a safe therapeutic relatively free of fungal infection or other side-effects, compared to synthetic medicines. In addition, the known physiological activities of the extracts from *Trachelospermi Caulis* and *Paeonia Suffruticosa* Andrews including antibacterial activity, bone reinforcement, antiphlogistic activity, blood nourishment, vigoration, etc. may bring about a synergistic effect on the prevention, treatment and improvement of an inflammatory disease.

8 Claims, 13 Drawing Sheets

(56) References Cited

FOREIGN PATENT DOCUMENTS

| WO | 2008/091064 A1 | 7/2008 |
|---|---|---|
| WO | 2010/036065 A2 | 4/2010 |

OTHER PUBLICATIONS

Jonat et al. (2004) Powder Technology 141: 31-43.*
Kim et al. (2012) JPP 64 pp. 420-429.*
Qian et al. (2012) J. Pharm. Sci. 101: 444-463.*
Stulzer et al. (2008) J. Thermal Anal. and Calorimetry, vol. 91, 1, 323-328.*
International Search Report for PCT/KR2011/006094, mailed on Mar. 23, 2012.
Written Opinion for PCT/KR2011/006094, mailed on Mar. 23, 2012.
Hong et al., "Inhibitory Effects of Paeonia *suffruiticosa* on Allergic Reactions by Inhibiting the NF-kappaB/IkappaB-alpha Signaling Pathway and Phosphorylation of ERK in an Animal Model and Human Mast Cells," *Biosci. Biotechnol. Biochem.*, 74(6):1152-1156 (2010).
Kim et al., "Effect of Moutan Cortex on Collagen-induced Arthritis," *The Journal of Traditional Korean Medicine*, 7(2):60-69 (2007).
Oh et al., "Inhibitory effects of the root cortex of Paeonia *suffruiticosa* on interleukin-8 and macrophage chemoattractant protein-1 secretions in U937 cells," *Journal of Ethnopharmacology*, 84:85-89 (2003).
Chung et al., "Inhibition of Nitric Oxide and Tumor Necrosis Factor-Alpha by Moutan Cortex in Activated Mouse Peritoneal Macrophages," Biol. Pharm. Bull. 30(5) 912-916, 2007.
Zhang et al., "Paeoniflorin suppresses inflammatory mediator production and regulates G protein-coupled signaling in fibroblast—like synoviocytes of collagen induced arthritic rats," Inflamm. Res. 57: 388-395, 2008.

* cited by examiner

Fig. 5
(a)
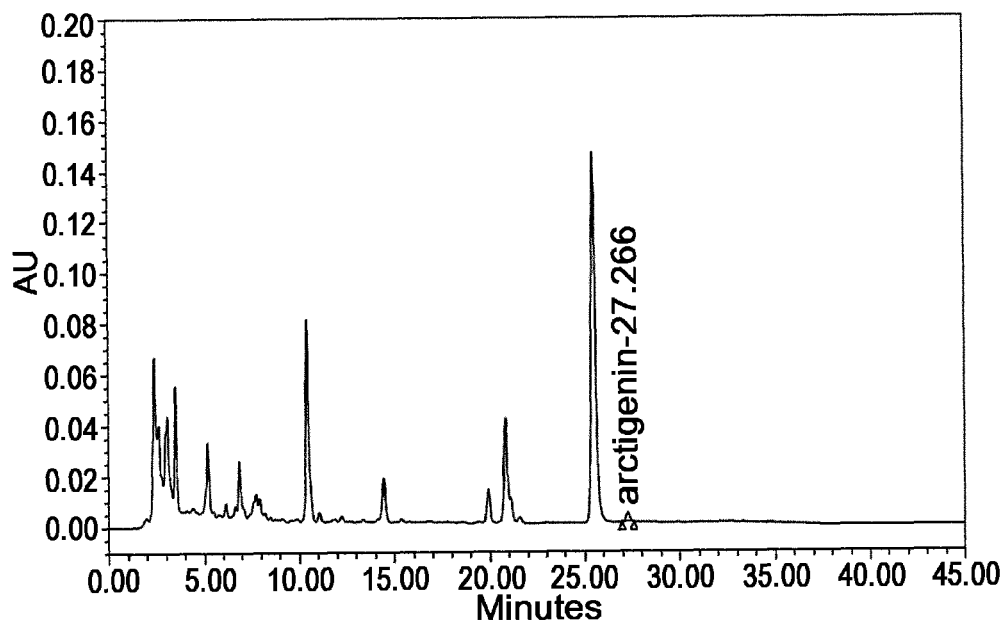
(b)
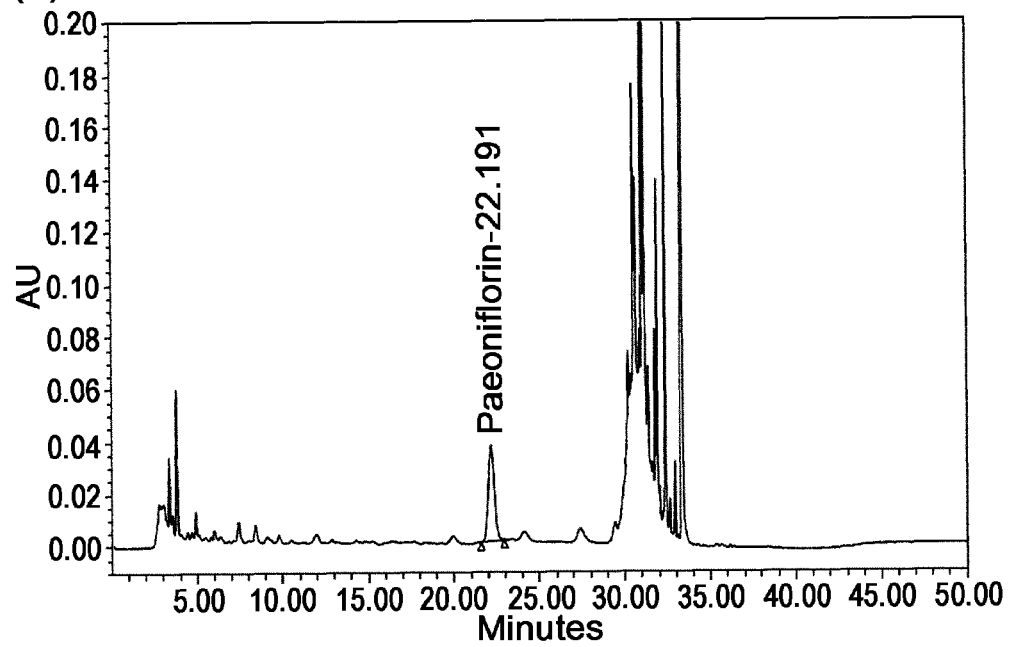

Fig. 9
Inhibition of IL-6-induced STAT3 phosphorylation
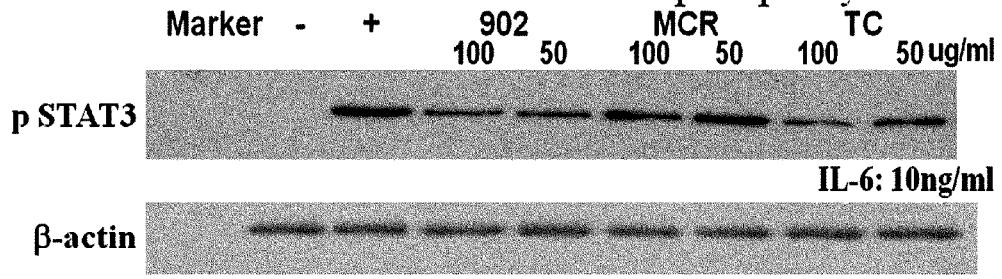
IL-6: 10ng/ml
PMA induced ERK phosphorylation
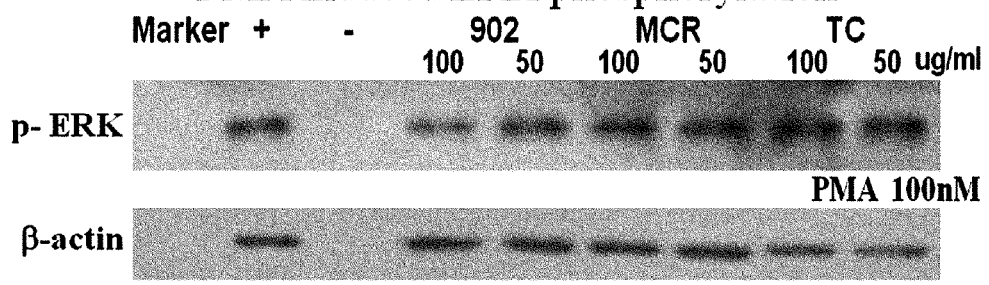
PMA 100nM
IL-6 induced JAK2 phosphorylation
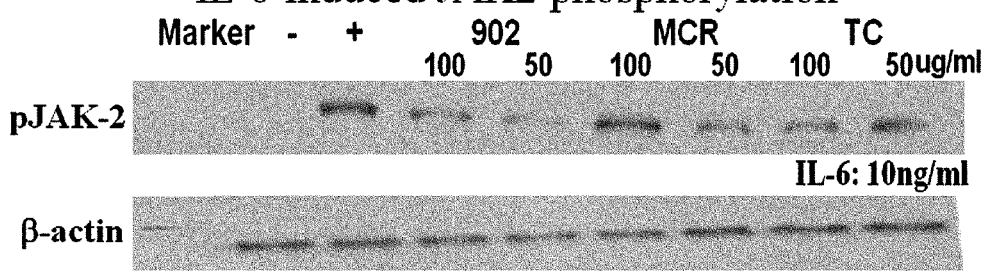
IL-6: 10ng/ml
IL-6 induced gp130 phosphorylation
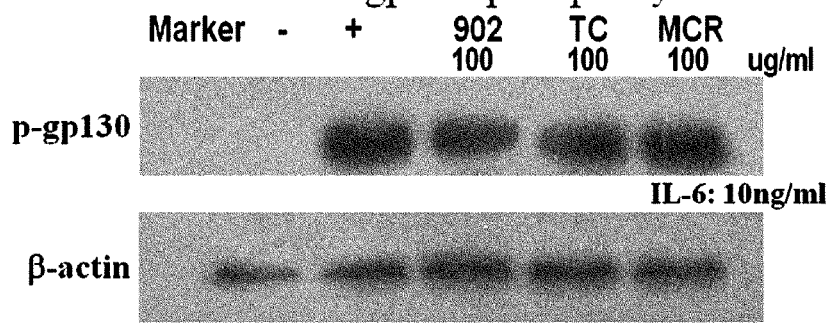
IL-6: 10ng/ml Fig. 13
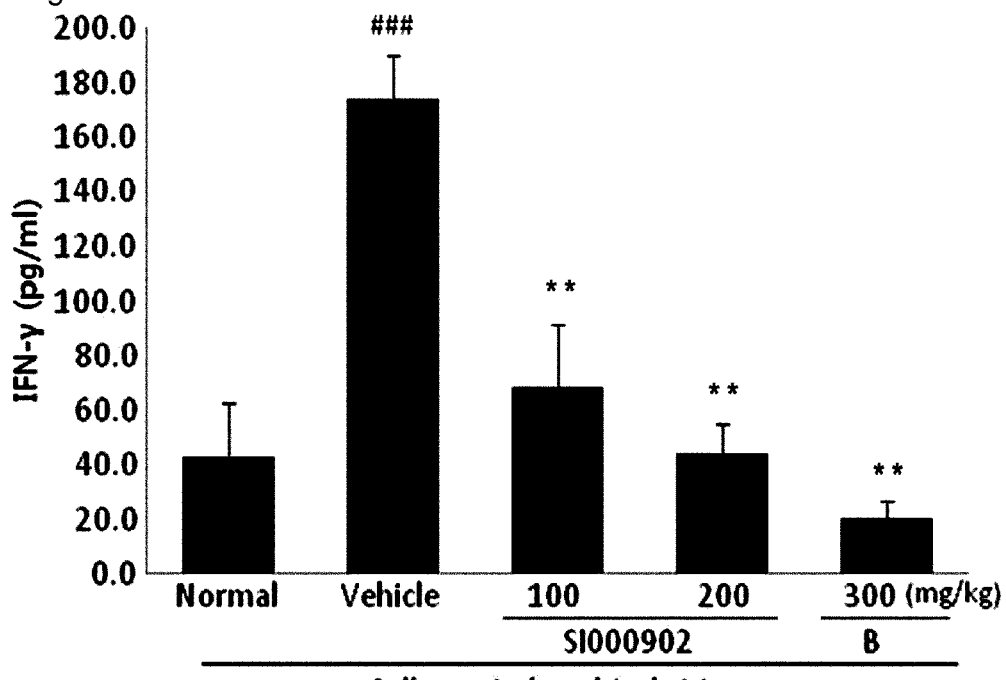
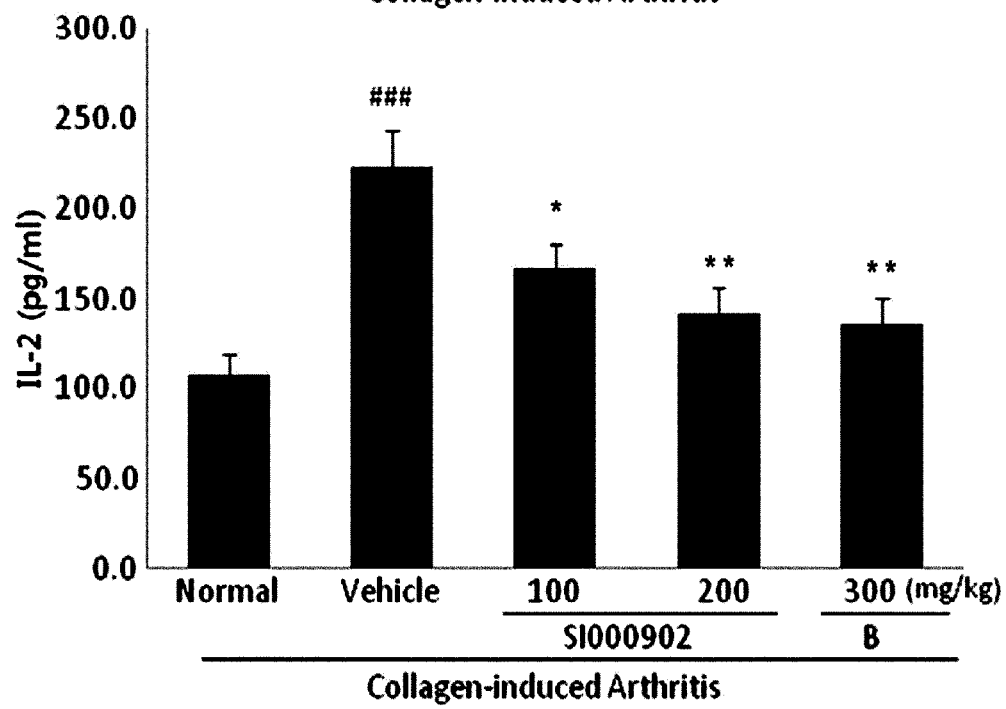

PHARMACEUTICAL COMPOSITION FOR PREVENTING OR TREATING INFLAMMATORY DISEASES COMPRISING TRACHELOSPERMI CAULIS EXTRACT AND PAEONIA SUFFRUTICOSA ANDREWS EXTRACT, AND METHOD FOR PREPARING THE SAME

CROSS-REFERENCES TO RELATED APPLICATIONS

This application is a U.S. national phase application of International PCT Patent Application No. PCT/KR2011/006094, which was filed on Aug. 18, 2011, which claims priority to Korean Patent Application Nos. 10-2010-0123086, filed Dec. 3, 2010; 10-2011-0072020, filed Jul. 20, 2011; 10-2011-0072011, filed Jul. 20, 2011. These applications are incorporated herein by reference in their entireties.

TECHNICAL FIELD

The present invention relates to a pharmaceutical composition for preventing or treating an inflammatory disease, comprising a mixture of extracts from *Trachelospermi Caulis* and *Paeonia Suffruticosa* Andrews as an active ingredient and method for preparing the same. Also, the present invention relates to a quasi-drug composition, a health functional food composition, and a cosmetic composition for preventing or improving inflammation, comprising a mixture of extracts from *Trachelospermi Caulis* and *Paeonia Suffruticosa* Andrews as an active ingredient. In addition, the present invention relates to a method for treating an inflammatory disease, comprising administering the pharmaceutical composition to a subject suspected of having the inflammatory disease.

BACKGROUND ART

An inflammatory disease is a generic name for diseases having inflammation as their main damaging factor. Inflammation, which is a biological response of tissue to harmful stimuli, is a lesion with the concurrence of the three events of tissue degradation, circulatory disturbance and fluid exudation, and hypertrophy. Examples of the inflammatory disease include acute and chronic disease, concretely, but are not limited to, edema, dermatitis, allergy, atopy, asthma, conjunctivitis, peridontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatoid arthritis, periarthritis of shoulder, tendonitis, tenosynovitis, myositis, hepatitis, cystitis, nephritis, sjogren's syndrome and multiple sclerosis.

A joint is the location at which two or more bones make contact, typically comprising cartilagenous tissue which functions as a shock absorber. Arthritis is a form of joint disorder that involves inflammation of one or more joints. It is a kind of chronic disease accompanied by the generation of edema, pain and stiffness at the joint affected. In a severe case, arthritis causes disability. Particularly, rheumatoid arthritis is progressive for life in most, causing articular deformity. Often, the absence of effective treatment and the aggregation of the disease result in severe physical disability. The reports of the Center for Disease Control and Prevention (CDC) and the Arthritis Foundation (AF) have it that in the United States, arthritis and other rheumatic conditions were estimated to affect more than 43 million people, corresponding to one fifth of the population, in 1997 and are projected to affect 70 million by 2020, one third of the 2020 population, adding that the number of patients with arthritis will continuously increase with aging of the population. In Korea, it is estimated that as many as 10 million people were affected by arthritis in 2005. There are various forms of arthritis according to its causes although having similar inflammatory symptoms at the joint. The mostly prevalent forms are osteoarthritis (degenerative joint disease) and rheumatoid arthritis. Other arthritis forms include gout and ankylosing spondylitis. Forms of arthritis are classified in Table 1, below.

TABLE 1

| Classification | Causes and Symptoms |
| --- | --- |
| Osteoarthritis(Degenerative arthritis) | Aging |
| Rheumatoid arthritis | Abnormality of immune response |
| Gouty arthritis | Increased level and accumulation of uric acid due to abnormal purine metabolism |
| Ankylosing spondylitis | Caused by genetic predisposition, or bacterial or viral infection, inflammation at the spine |
| Infectious arthritis | Articular tissues infected by pathogens |
| Juvenile idiopathic arthritis | The onset of rheumatoid arthritis before age 16 |
| Achillobursitis | Inflammation around the Archille's tendon |

Rheumatoid arthritis is a chronic, systemic inflammatory disease that may affect many tissues and organs, but principally attacks synovial joints. Autoimmunity, that is, an excessive immune response against autologous cells, plays a pivotal role in both chronicity and the progression of rheumatoid arthritis. Inflammation occurs in the cells attacked by the immune system. With time, rheumatoid arthritis nearly always affects multiple joints, most commonly the small joints of the hands, feet and cervical spine, but larger joints like the elbows, hip joints and knees can also be involved. The onset is most frequent in women between the ages of 25 and 50, with physical disability following within 10 years after onset.

After onset, rheumatoid arthritis progresses in concert with the formation of granulation tissue, known as 'pannus', at the edges of the synovial lining, which leads to the destruction of articular cartilage, the deformation of the joint, and the weakening of the bones of the joint. The synovial tissue with pannus produces and releases various pro-inflammatory molecules including cytokines, chemokines and the like. Also, the tissue has been recently reported to release a lot of IL-6 and IL-8, known to be involved in the damage and destruction of joints, as well as TNF-α, IL-1β, IL-15 and IL-18. Several cell types have been implicated as major contributors in the patho-physiological process of rheumatoid arthritis, including T cells, B cells, macrophages, synoviocytes and chondrocytes, and they form a division in the joint, producing rheumatoid arthritis inducers that damage articular cartilages and bones.

There are various synthetic compounds that have been developed as medicines for rheumatoid arthritis. However, the FDA ordered the pharmaceutical companies to add a new black box warning to Enbrel, Humira, Remicade and Cimzia about the increased risk of potentially deadly fungal infections. The FDA pointed out that the TNF blockers, although alleviating the pain of the swelling joint, suppress the immune system to make the body vulnerable to various infections, particularly warning the onset of histoplasmosis in people taking the drugs. The FDA has received 240 reports of patients taking TNF blockers who developed histoplasmosis. Among the 240 patients, 45 patients, which correspond to as many as about 20% of those affected, died, including at least 12 who were not diagnosed with histoplasmosis right away. Besides, the Korean Food and Drug Administration (KFDA) announced that a letter, in relation with the death of 130 persons taking a rheumatoid arthritis medicine in Japan, was transmitted to the Korean Medical Association and the Korean Pharmaceutical Association about the side effect of the drug, emphasizing that when taking methotrexate, used as an active ingredient of a medication for arthritis, the patient must be issued with instructions by the attending physicians and pharmacists because the ingredient is likely to cause serious adverse effects such as interstitial pneumonia and bone marrow suppression. Known and unknown, but likely side effects of synthetic medicines for rheumatoid arthritis, such as fungal infections, etc., have recently directed research and development toward natural herbal ingredients that can be safely used in the treatment of rheumatoid arthritis. As a result, several rheumatoid arthritis medicines made of herbal ingredients have been introduced.

Conventional arthritis medicines include non-steroidal inflammatory drugs (NSAIDS), which are expected to bring about pain relief only, adrenocortical hormone agents, which show anti-inflammatoy activity and therapeutic effects, and antirheumatic drugs, which can treat rheumatic arthritis. Representative among the antirheumatic drugs are the immunomodulators such as penicillamine and bucillamine, the immunosuppressants such as cyclosporine, azathioprine, methotrexate and gold salts, and the antimalarial agent hydroxychloroquine, two or more of which are commonly used in combination. For the last five years, many changes have occurred in arthritis medicines. Like TNF blockers and COX-2 inhibitors, drugs which control pain and prevent the generation of many complications have been developed. In scenarios of inflammation, a lot of prostaglandins, a group of lipid compounds, which are inflammatory mediators, are biosynthesized from arachidonic acid, in which cyclooxygenase (COX) is involved. NSAIDS, widely used to treat most inflammatory diseases, function to inhibit the COX enzyme to prevent the biosynthesis of prostaglandins.

Because they employ herbal extracts as their active ingredient, most of the medicines for arthritis are based on natural materials and their accurate pharmaceutical mechanism remains unknown. However, they are actively being developed as oral formulations which are easy to administer and which can be administered for a long period of time. As a natural material, hyaluronic acid, similar to synovial fluid, is injected. As a helper for health functional food, glucosamine is ingested possibly in combination with chondroitin. The development of useful medicines of natural materials may refer to the ancient publications of herbal medicine, such as Tong-Ui-Bo-Gam.

With the great advances in molecular biological technology, the medicinal effects and safety of natural materials have been revealed, and natural medicines are being reviewed from different angles. Now, natural medicines are recognized as special medicines thanks to their advantage of producing no adverse effects even after long-term ingestion. Usually, natural medicines have been developed by utilizing medicinally effective ingredients alone or in combination, and are extracted and isolated from herbs and/or animals which are ingested as food. Having low toxicity compared to synthetic medicines, natural medicines are regarded as being highly safe.

However, natural medicines also have many problems, particularly upon formulation. For example, a dried powder of herbal extract is difficult to handle because it absorbs lots of moisture. Even when it is formulated into a solid oral form, natural medicine is difficult to maintain for a long period of time in terms of morphology and content because it absorbs a lot of moisture when in a formulation.

In the body, various biochemical events account for the onset of inflammation. In response to chemical stimuli, macrophages produce various cytokines and nitric oxide (NO) that play an important role in the inflammatory process. As a result of the inflammatory processes, the supraphysiological concentrations of nitrogen oxide produced by iNOS (inducible nitric oxide synthase) play a major role in the pathobiology of various inflammatory diseases (Kobayashi Y. et al., J Leukoc Biol., 88, pp 1157-62, 2010). In addition, various studies have shown that interleukin-6(IL-6) and interleukin(IL-1β) are a kind of cytokine promoting the inflammatory responses (Punzi L. et al., Crit Rev Clin Lab Sci., 2002, 39(1):63-88), which is known to account for the onset of various inflammatory diseases including rheumatoid arthritis (fang C. H. et al., Rheumatology, 2006, 45(6):703-710), fibromyalgia (Hernandez M. E. et. al., BMC Res. Notes., 2010, 3(1):156), and sjogren's syndrome (Baturone R. et. al., Scand J Rheumatol., 2009, 38(5):386-389). These research results indicate that if it has the function of inhibiting the production of nitric oxide (NO) or cytokines such as IL-6, and IL-1β, a material might be effectively used to prevent and treat various inflammatory diseases.

DISCLOSURE OF INVENTION

Technical Problem

Leading to the present invention, intensive and thorough research into phytochemicals effectively therapeutic of inflammation or arthritis, conducted by the present inventors, resulted in the finding that a combination of extracts from *Trachelospermi Caulis* and *Paeonia Suffruticosa* Andrews has the activity of controlling and suppressing factors involved in the expression of the mediators of rheumatoid arthritis, thus being useful for the prevention, treatment and improvement of inflammatory diseases, and in developing a formulation which can be stable in combined extracts, thus solving the problems of moisture absorbance, material density, fluidity, adhesive aggregation, etc.

Solution to Problem

It is therefore an object of the present invention to provide a pharmaceutical composition for preventing or treating an inflammatory disease, comprising a mixture of a *Trachelospermi Caulis* extract and a *Paeonia Suffruticosa* Andrews extract as an active ingredient.

It is another object of the present invention to provide a quasi-drug composition for preventing or improving inflammation, comprising a mixture of a *Trachelospermi Caulis* extract and a *Paeonia Suffruticosa* Andrews extract as an active ingredient.

It is a further object of the present invention to provide a health functional food composition for preventing or improving inflammation, comprising a mixture of a *Trachelospermi Caulis* extract and a *Paeonia Suffruticosa* Andrews extract as an active ingredient.

It is still a further object of the present invention to provide a cosmetic composition for preventing or improving inflammation, comprising a mixture of a *Trachelospermi Caulis* extract and a *Paeonia Suffruticosa* Andrews extract as an active ingredient.

It is still another object of the present invention to provide a method for preparing a composition for preventing or treating an inflammatory disease, comprising: (a) extracting *Trachelospermi Caulis* in an aqueous ethanol solution, followed by filtering to separate filtrate and remnant, and drying the filtrate to obtain an extract containing arctigenin in an amount of from 0.05 to 1.5 wt %, the arctigenin serving as an index substance for *Trachelospermi Caulis*; (b) extracting *Paeonia Suffruticosa* Andrews in an aqueous ethanol solution, followed by filtering to separate filtrate and remnant, and drying the filtrate to obtain an extract containing paeoniflorin in an amount of from 1.8 to 5.3 wt %, the paeoniflorin serving as an index substance for *Paeonia Suffruticosa* Andrews; and (c) mixing the *Trachelospermi Caulis* extract of step (a) and the *Paeonia Suffruticosa* Andrews extract of step (b) at a ratio of 1:1 to 3:1, based on dry weight to obtain a mixture.

It is still yet a further object of the present invention to provide a method for treating an inflammatory disease, comprising administering the pharmaceutical composition to a subject suspected for the inflammatory disease.

Advantageous Effects of Invention

Comprising a mixture of extracts from *Trachelospermi Caulis* and *Paeonia Suffruticosa* Andrews, the composition of the present invention exhibits excellent anti-inflammatory activity and edema-suppressing activity, compared to individual extracts, and thus can be applied to the prevention, treatment or improvement of inflammatory diseases. As natural materials, the composition can be used as a safe therapeutic relatively free of fungal infection or other side-effects, compared to synthetic medicines. In addition, the known physiological activities of the extracts from *Trachelospermi Caulis* and *Paeonia Suffruticosa* Andrews including antibacterial activity, bone reinforcement, antiphlogistic activity, blood nourishment, vigoration, etc. may bring about a synergistic effect on the prevention, treatment and improvement of inflammatory diseases. When formulated into oral dosage forms, the composition guarantees a sufficient period of time to the manufacturing process. The formulation formed of the hygroscopicity-suppressed materials is also resistant to moisture so that it is advantageous in terms of storage and administration.

BRIEF DESCRIPTION OF DRAWINGS

FIG. 5 is of HPLC chromatograms of the mixture of extracts from *Trachelospermi Caulis* and *Paeonia Suffruticosa* Andrews.

FIG. 9 is a graph showing the inhibitory activities of a *Trachelospermi Caulis* extract (TC), a *Paeonia Suffruticosa* Andrews extract (MCR), and a mixture of extracts from *Trachelospermi Caulis* and *Paeonia Suffruticosa* Andrews (SI-000902) against IL-6-induced signal pathway (JAK2 phosphorylateion, gp130 phosphorylation and STAT3 phosphorylation) and PMA-induced ERK phosphorylateion.

FIG. 13 is of graphs showing inhibitory effects of a mixture of soft extracts of *Trachelospermi Caulis* and *Paeonia Suffruticosa* Andrews (SI-000902) and bucillamine (B) on the production of IFN-γ and IL-2 of splenocytes of arthritis-induced mice.

BEST MODE FOR CARRYING OUT THE INVENTION

Figure 1:
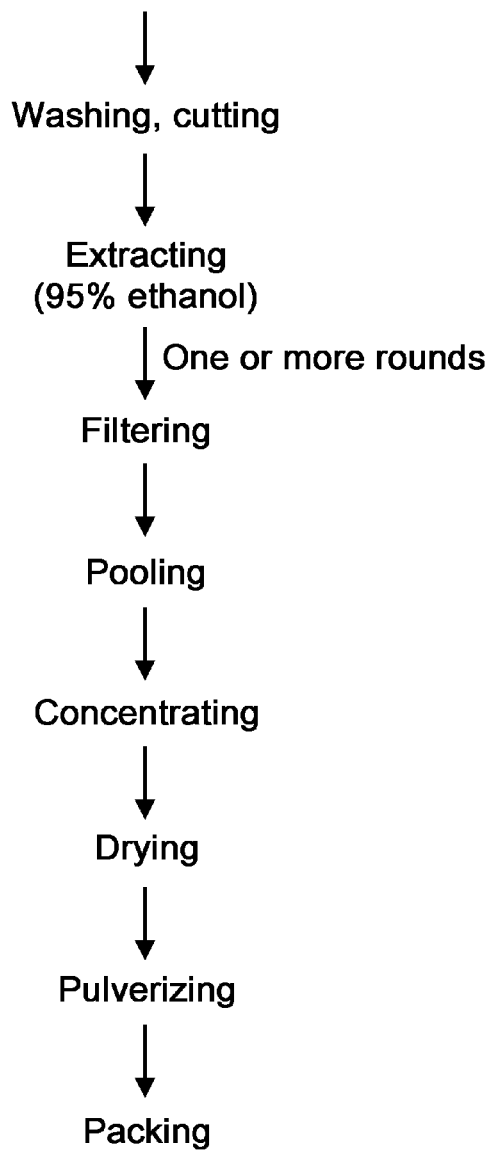
FIG. 1 is a process flow showing the preparation of a 95% ethanol solid extract from *Trachelospermi Caulis* and *Paeonia Suffruticosa* Andrews.

In accordance with an aspect thereof, the present invention provides a pharmaceutical composition for preventing or treating an inflammatory disease, comprising a mixture of a *Trachelospermi Caulis* extract and a *Paeonia Suffruticosa* Andrews extract as an active ingredient.

As used herein, the term "*Trachelospermi Caulis*", known as climbing bagbane, refers to climbing stems and branches of *Trachelospermum asiaticum* or its closely related plants (Apocyanaceae). In Korean ancient medicinal publications, an extract from the herb is described as functionally acting on the heart, the liver and the kidney to treat diseases caused by wind and dampness, and to help the flow of the life-energy through the meridian system and is prescribed for splenosis, limb convulsion, lumbago, arthralgia, tonsillitis, and boils. Arctiin, arctigenin, tracheloside, matairesinoside, and cymarose, found thus far as physiologically active ingredients in *Trachelospermi Caulis*, are known to have vasodilative and anti-hypertensive activity.

The term "*Paeonia suffruticosa* Andrews," known as peony, as used herein, refers to the root bark of peony. The root bark is non-toxic to the body and is used as a medicinal material in herbal medicine. The physiologically active ingredients found in the herb include paeonoside (paeonol glucoside), paeonolide (paeonol-rhamnoglucoside) and paeonol. During the storage of the herb, paeonoside is degraded into sugar and paonol. In addition, paeoniflorin, oxypaeoniflorin, benzoylpaeoniflorin, paeonolide tannin, procyanidin B1, benzoyloxypaeoniflorin, paeonin, astragalin, and pelargonin are detected. Histochemistry showed that these ingredients are present in the lignin as well as the root bark. In herbal medicine, a *Paeonia suffruticosa* Andrews extract is prescribed as a therapeutic for extravasated blood, which is estimated to be attributed to the anti-inflammatory activity of its monoterpene glycosides. Showing anti-bacterial activity, paeonol was observed to inhibit *E. coli, staphylococci, streptococci* and *Bacillus subtilis* in vitro even when it was 1,500- to 2,000-fold diluted. Benzoylpaeoniflorin and benzoyloxypaeoniflorin function to suppress the release of histamine from mast cells while paeonolide tannin shows anti-viral activity. Paeoniflorin inhibits the aggregation of platelets and reduces the level of fibrinogen. In herbal medicine, *Paeonia suffruticosa* Andrews, classified as having a cold predisposition, is used as a medicine for anti-phlogistics and extravasated blood and thus is prescribed for vascular inflammation in the hypergastric organs, a sharp pain due to the congestion of blood, fever, suppuration, and hemorrhage, particularly for gynecologic diseases including menstrual irregularity and inflammation, congestion of blood, and a dull pain in the uterus and uterine adnexa. Also, pain relief and spasmolysis are applied to the treatment of hemorrhoids and appendicitis.

As mentioned above, the pharmaceutical composition of the present invention features the anti-inflammatory activity of a mixture of extracts from *Trachelospermi Caulis* and *Paeonia Suffruticosa* Andrews. The extract mixture may be obtained by preparing a *Trachelospermi Caulis* extract and a *Paeonia Suffruticosa* Andrews extract, separately, and mixing them in a predetermined ratio. The weight ratio, based on dried weight, between the *Trachelospermi Caulis* extract and the *Paeonia Suffruticosa* Andrews extract may be preferably 1:1 to 3:1 and more preferably 1:1. In addition, the amounts of the extracts from *Trachelospermi Caulis* and *Paeonia Suffruticosa* Andrews may be determined depending on the contents of their respective index substances Arctigenin and paeoniflorin. In this case, the mixture may contain arctigenin in an amount of from 0.05 to 1.5 wt % and paeoniflorin in an amount of from 1.8 to 5.3 wt %. Compared to individual extracts from *Trachelospermi Caulis* or *Paeonia Suffruticosa* Andrews, the extract mixture guarantees a pharmaceutical composition for the prevention and treatment of inflammatory diseases, which is superior in terms of analgesic activity, inhibitory activity against acute and chronic inflammation and against the release of nitric oxide and inflammatory cytokines.

In one embodiment, the inhibitory activity against nitric oxide and cytokines of the extract mixture was measured to be higher than or similar to that of individual extracts even when the extract mixture was used at half of the concentration of individual extracts. Particularly, the extract mixture, when used in combination, was identified to have a synergistically inhibitory effect on IL-1β production and IL-6-induced JAK2 and STAT3 phosphorylation that facilitates the differentiation of B cells, and thus are mutually complementary without interfering or obstructing their own activities (FIGS. 6 to 9).

Each of the extracts from *Trachelospermi Caulis* and *Paeonia Suffruticosa* Andrews may be an extract obtained by an extraction process, a dilution or concentration of the extract, a residue after drying the extract, a coarse filtrate of the extract, or a fine filtrate, but the present invention is not limited thereto. Individuals of the extracts may be obtained using a typical extraction solvent and preferably using one selected from the group consisting of water, an alcohol of 1 to 6 carbon atoms or a combination thereof. The alcohol may be preferably ethanol, methanol or butanol, and more preferably a 90% to 99% ethanol solution.

Each of the extracts from *Trachelospermi Caulis* and *Paeonia Suffruticosa* Andrews includes, but is not limited to, an ethanol solid extract or soft extract.

As used herein, the term "solid extract" means an agent prepared by immersing an herbal material in a suitable solvent to allow useful ingredients to leach into the solvent by cold precipitation, warm precipitation or percolation, followed by concentrating and drying the leachate in a suitable manner. The solid extract may be processed into lumps, particulates or powders. In one embodiment of the present invention, *Trachelospermi Caulis* and *Paeonia Suffruticosa* Andrews were washed, extracted with 95% ethanol, and filtered, and the filtrates were pooled, concentrated, dried and pulverized to obtain a solid extract (FIG. 1).

Figure 2:
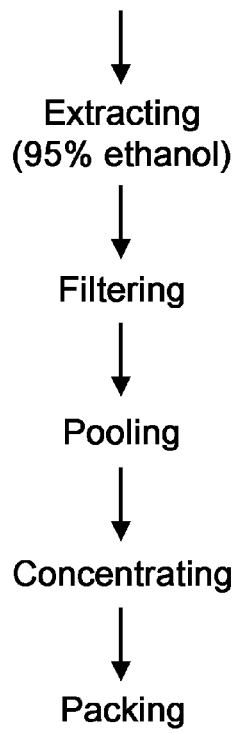
FIG. 2 is a process flow showing the preparation of a 95% ethanol soft extract from *Trachelospermi Caulis* and *Paeonia Suffruticosa* Andrews.

The term "soft extract," as used herein, means an agent prepared by immersing an herbal material in a suitable solvent (purified water, ethanol and so on) to allow useful ingredients to leach into the solvent, followed by concentrating the leachate to form a syrup. In one embodiment of the present invention, *Trachelospermi Caulis* and *Paeonia Suffruticosa* Andrews were washed, extracted with 95% ethanol and filtered and the filtrates were pooled and concentrated to obtain a soft extract (FIG. 2).

Arctigenin, selected as an index substance for *Trachelospermi Caulis*, has an empirical formula of $C_{21}H_{24}O_6$ with a molecular weight of 372 and functions as a dibenzylbutyroactone ligand. Its physiological activity in various plants is being actively studied, especially in composite plants. The compound is an important ingredient in medicines for inflammatory diseases and can exhibit a potential medicinal efficacy, contributing to the synergistic effect when its content is limited to a certain range. In the pharmaceutical composition, the content of arctigenin preferably ranges from 0.03 to 2.0 wt % and more preferably from 0.05 to 1.5 wt %.

Paeoniflorin, selected as an index substance for *Paeonia Suffruticosa* Andrews, has an empirical formula of $C_{23}H_{28}O_{11}$ with a molecular weight of 480.45 and is an important ingredient found in the root of the peony. The compound, also called peony saponin, is a colorless, crystalline substance and is known to have the effects of expanding blood vessels, fighting against inflammation and hypersensitiveness and promoting immune activity. The pharmaceutical composition of the present invention may preferably contain paoniflorin in an amount of from 1.4 to 5.5 wt % and more preferably in an amount of from 1.8 to 5.3 wt %.

In one embodiment of the present invention, extracts from *Trachelospermi Caulis* and *Paeonia Suffruticosa* Andrews which were gathered from different sites and at different times, were found to contain arctigenin in an amount of from 0.05 to 1.5 wt % and paeoniflorin in an amount of from 1.8 to 5.3 wt %.

Figure 6:
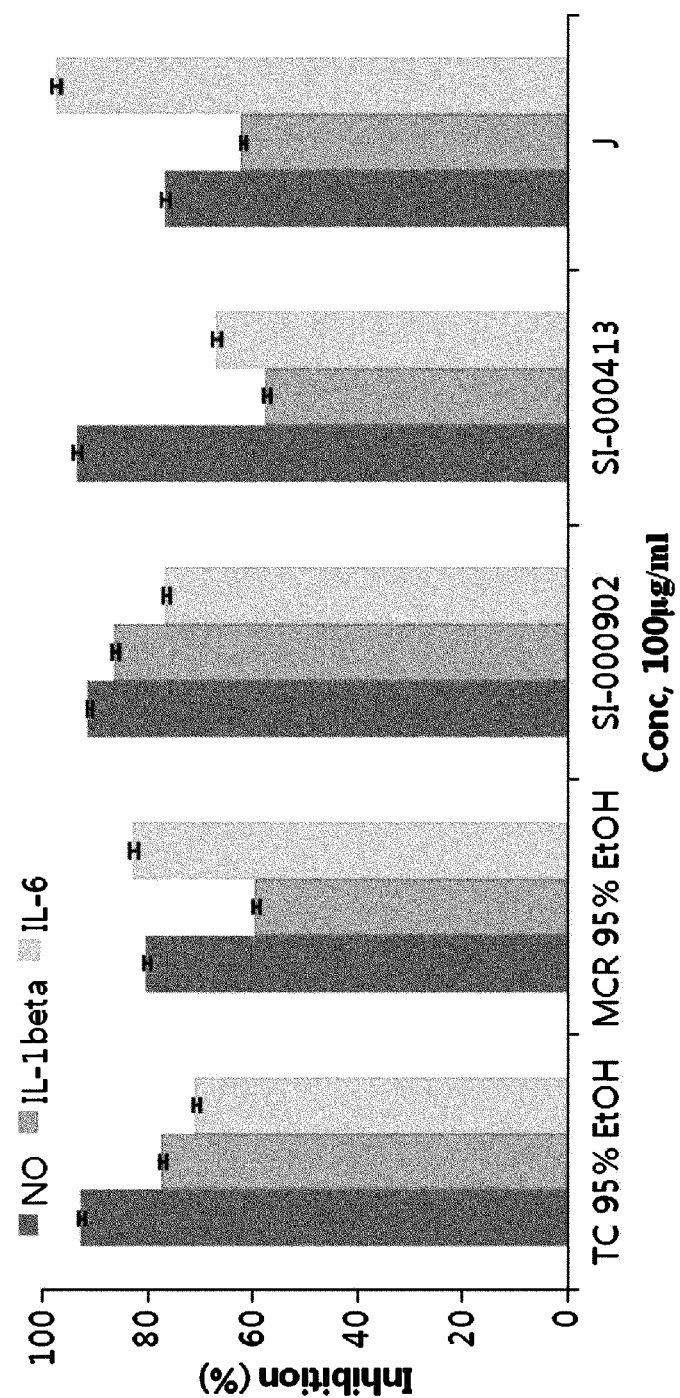
FIG. 6 is a graph showing the inhibitory activities of a *Trachelospermi Caulis* extract (TC), a *Paeonia Suffruticosa* Andrews extract (MCR), a mixture of extracts from *Trachelospermi Caulis* and *Paeonia Suffruticosa* Andrews (SI-000902), a composite herbal medicine (SI-000413) and a Joins tablet (J) against the release of nitric oxide (NO), IL-1β and IL-6 when each of them is applied in a concentration of 100 μg/mL to mouse-derived macrophage RAW 264.7.

The composition of the present invention is characterized by the ability to inhibit the release of the inflammatory factors nitric oxide (NO), IL-6 or IL-1β. The composition exhibits prophylactic or therapeutic effects on inflammatory diseases by suppressing the release of nitric oxide and the inflammatory cytokines IL-6 and IL-1β. In one embodiment of the present invention, a mixture of the extracts from *Trachelospermi Caulis* and *Paeonia Suffruticosa* Andrews was observed to have excellent inhibitory activity against nitric oxide and inflammatory cytokines (FIG. 6).

The term "inflammatory disease," as used herein, is a generic name of the diseases having inflammation as their main damaging factor. Examples of the inflammatory disease include, but are not limited to, edema, dermatitis, allergy, atopy, asthma, conjunctivitis, peridontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatoid arthritis, periarthritis of shoulder, tendonitis, tenosynovitis, myositis, hepatitis, cystitis, nephritis, sjogren's syndrome and multiple sclerosis, with a preference for rheumatoid arthritis and edema, the former being more strongly preferred.

Arthritis is a collective term for a disease associated with inflammatory changes which occur within a joint region due to bacterial infection or external injuries. Arthritis is largely classified into acute arthritis and chronic arthritis. Acute arthritis is further divided as follows. (1) Serous arthritis: commonly caused by external injuries, but may occur for unknown reasons. It generally occurs in one joint. (2) Serofibrinous arthritis: this occurs with the acute rheumatoid arthritis, and a turbid effusion gathers in the articular cavity. This may cause dyscinesia due to the generation of a pseudomembrane even after inflammation abates. (3) Suppurative arthritis: multiple occurrences of arthritis in the open wounds of a joint or contagious diseases such as gonorrhea, typhoid, scarlatinal, and septicemic. Young infants 1-2 months old may develop abarticulation due to the uncurable severe damage to the bones. Adults often develop periosteomyelitis which cause rupture and allows pus to flow into joints, so called secondary suppurative arthritis. Chronic arthritis can be further divided as follows. (1) Specific type of inflammation: generally refers to a gouty arthritis caused by tuberculous arthritis or syphilitic arthritis or a metabolic disorder of uric acid commonly occurring in middle aged men. (2) Multiple arthritis: chronic rheumatoid arthritis is most common. Acute serous arthritis may transform into multiple arthritis, or it may occur as a polyarthritis in the course of pneumonia, syphilis, and gonorrhea, or it may be a kind of septicemia. In addition, Still's disease also belongs to this category. (3) Arthritis deformans: generally caused by degenerative aging process or external injuries. (4) Hemophiliac arthritis: caused by bleeding in the joints in a hemophiliac patient. Degenerative arthritis, also called osteoarthritis, is a local arthritis resulting from a degenerative change in the joint cartilage, and occurs mainly in middle aged or senior people. Such arthritis causes an elevated level of inflammatory cytokines and nitric oxide.

Rheumatoid arthritis is a chronic, systemic inflammatory disease that may affect many tissues, and its cause remains unknown. The process initially produces an inflammatory response of the synovial membrane surrounding the joint, which then gradually spreads to adjacent cartilage and bones, leading to destruction and deformation of the joint. Extra-articular manifestations include anemia, sicca syndrome, subcutaneous nodule, pulmonary fibrosis, vasculitis, dermal ulcer, etc. In one embodiment of the present invention, a mixture of the extracts from *Trachelospermi Caulis* and *Paeonia Suffruticosa* Andrews was found to have a prophylactic and therapeutic effect on rheumatoid arthritis in vivo as measured using rheumatoid arthritis-induced mice as an animal model.

Edema is an abnormal accumulation of fluid, such as lymph or exudates, beneath the skin or in one or more cavities of the body. Upon the onset of edema, the affected skin or soft tissue swells and becomes crispy to the touch. When pressed, a temporary indentation is made in the skin. In one embodiment of the present invention, a mixture of extracts from *Trachelospermi Caulis* and *Paeonia Suffruticosa* Andrews was found to have a prophylactic and therapeutic effect on edema as measured by an assay in which edemas in arthritis-induced mice were evaluated with the naked eye after the mixture was administered thereto. Generally, the mixture decreased the swelling of the feet of the test group.

As used herein, the term "prevention" or "prophylaxis" is intended to refer to any action resulting in the suppression or delay of the onset of inflammatory diseases thanks to the administration of the pharmaceutical composition according to the present invention. The term "treatment" is intended to refer to any action resulting in improvements in symptoms of inflammatory diseases or the beneficial alteration of the inflammatory state thanks to the administration of the composition according to the present invention.

The pharmaceutical composition of the present invention may further comprise a pharmaceutically acceptable vehicle. The pharmaceutical composition comprising a pharmaceutically acceptable vehicle may be in various oral or non-oral dosage forms. In this regard, the pharmaceutical composition of the present invention may be formulated in combination with diluents or excipient such as a filler, a thickener, a binder, a wetting agent, a disintegrant, a surfactant, etc. Solid preparations intended for oral administration may be in the form of tablets, pills, powders, granules, capsules, and the like. With regard to these solid agents, the compound of the present invention is formulated in combination with at least one excipient such as starch, calcium carbonate, sucrose, lactose, or gelatin. In addition to a simple excipient, a lubricant such as magnesium stearate, talc, etc. may be used. Among liquid preparations intended for oral administration are suspensions, internal use solutions, emulsion, syrups, and the like. In addition to a simple diluent such as water or liquid paraffin, various excipients, such as wetting agents, sweeteners, aromatics, preservatives, and the like may be contained in the liquid preparations. Also, the pharmaceutical composition of the present invention may be in a parenteral dosage form such as sterile aqueous solutions, non-aqueous solvents, suspensions, emulsions, lyophilizates, suppositories, and the like. Injectable propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

Further, the form of the dosage of the pharmaceutical composition of the present invention may be selected from the group consisting of a tablet, a pill, a powder, a granule, a capsule, a suspension, an internal use solution, an emulsion, a syrup, a sterile aqueous solution, a non-aqueous solution, a lyophilizate, and a suppository.

Extracts from *Trachelospermi Caulis* and *Paeonia Suffruticosa* Andrews have long been used as foods or medicinally, and no special limitations are placed on the dose of the extract mixture, but varies depending on various factors including in vivo absorption rate, patient's age, sex, health state and diet, the time of administration, the route of administration, excretion rate, and the severity of disease. Typically, the mixture of extracts from *Trachelospermi Caulis* and *Paeonia Suffruticosa* Andrews may be administered at a daily dose of from 10 to 1000 mg/kg and preferably at a daily dose of from 50 to 500 mg/kg. Preferably, the pharmaceutical composition of the present invention is formulated in consideration of the range of the amount that is effective. The unit dosage formulations thus obtained may be administered using a specialized regimen or at regular intervals of time in multiple doses according to the decision of an expert who is responsible for monitoring or observing the administration of the drug, or according to individual needs.

The pharmaceutical composition of the present invention may further comprise silicon dioxide and a pharmaceutically acceptable excipient for oral administration. The oral composition is effectively prevented from absorbing moisture.

Because both the *Trachelospermi Caulis* extract and the *Paeonia Suffruticosa* Andrews extract are of high hygroscopicity, a tablet formulation of the extract mixture may become too soft to maintain a tablet shape. A solution to this problem is to suppress the hygroscopicity of the active ingredients themselves to a maximal level. In this context, silicon dioxide and a pharmaceutically acceptable excipient are employed.

Silicon dioxide is employed to improve the hygroscopicity of both the *Trachelospermi Caulis* extract and the *Paeonia Suffruticosa* Andrews extract. Compared to microcrystalline cellulose or potassium silicate, which are usually used as excipients to block moisture absorption, silicon dioxide may be used in a significantly smaller amount and thus shows a much greater effect on the stabilization of the formulation and the index substances.

In one embodiment of the present invention, dried granules of the *Trachelospermi Caulis* extract or the *Paeonia Suffruticosa* Andrews extract were observed to be highly resistant to moisture at room temperature and to well maintain their morphology when containing silicon dioxide, compared to when not containing silicon dioxide and containing corn starch. Also, tests on disintegration and long-term stabilization show that tablets formed of the dried granules of the extract containing silicon dioxide maintained a disintegration time and the content of the active ingredients at a certain level even when they were stored under high-temperature and high-moisture conditions.

The employment of silicon dioxide suppresses the hygroscopicity of the active ingredients and allows the formulation to maintain its morphology, thus guaranteeing a large period of time enough to accurately complete the manufacturing process. The formulation formed of the hygroscopicity-suppressed materials is also resistant to moisture so that it is advantageous in terms of storage and distribution. Even when it is stored for a long period of time at a high temperature under a damp condition, the formulation ensures that the index substances stay stable, showing a constant release property (pharmacokinetics).

The pharmaceutical composition of the present invention may preferably comprise a mixture of the *Trachelospermi Caulis* extract plus the *Paeonia Suffruticosa* Andrews extract in an amount of 100 weight parts and silicon dioxide in an amount of from 30 to 100 weight parts. More preferably, 50 weight parts of silicon dioxide may be used. If the amount of silicon dioxide used is less than 30 weight parts based on 100 weight parts of the mixture of the *Trachelospermi Caulis* extract plus the *Paeonia Suffruticosa* Andrews extract, hygroscopicity is not sufficiently suppressed, thus bringing about only a slight stabilizing effect on the oral formulations. On the other hand, when an amount of silicon dioxide exceeds 100 weight parts, the tablet becomes large, and a relatively large amount of non-active substances is apt to cause a side effect. In addition, the surplus amount brings about only a slight stabilizing effect on the formulation.

The term "pharmaceutically acceptable excipient," as used herein, comprehensively means a vehicle that is pharmaceutically accepted. The excipient for oral formulations include a diluent, a filler, a thickener, a binder, a wetting agent, a disintegrant, a surfactant, a lubricant, a colorant and a fragrant, but is not limited thereto. Preferably, the excipient may be microcrystalline cellulose or potassium silicate. Like silicon dioxide, microcrystalline cellulose or potassium silicate can function to absorb moisture from the extracts from *Trachelospermi Caulis* and *Paeonia Suffruticosa* Andrews, more readily facilitating the formation of solid formulations.

The microcrystalline cellulose or potassium silicate may be preferably used in an amount of from 10 to 50 weight parts based on 100 weigh parts of the mixture of extracts from *Trachelospermi Caulis* plus *Paeonia Suffruticosa* Andrews. When used in an amount less than 10 weight parts, microcrystalline cellulose or potassium silicate shows slight synergistic effect on hygroscopicity, together with silicon dioxide. An amount exceeding 50 weight parts makes the tablet large in size and brings about no positive effects on the stability of formulation.

The oral dosage forms of the pharmaceutical composition of the present invention include, but are not limited to, powders, granules, fillers, soft capsules, tablets, and suspensions, with preference for powders, granules, soft capsules or tablets. The moisture content of the tablets is preferably 4 to 6%, and more preferably 5%.

In accordance with another aspect thereof, the present invention provides a quasi-drug composition for preventing or improving inflammation, comprising the mixture of extracts from *Trachelospermi Caulis* and *Paeonia Suffruticosa* Andrews as an active ingredient. As for the mixture of extracts from *Trachelospermi Caulis* and *Paeonia Suffruticosa* Andrews compound, its description is as given above. In greater detail, the composition of the present invention may be added to a quasi-drug composition to be used to prevent or improve inflammation.

As used herein, the term "quasi-drug" may be defined as articles made from fiber, rubber, or similar materials used in humans or animals for the purpose of curing, alleviating, treating, or preventing diseases; articles, other than instruments, machines or the like, which have a mild action on or have no direct influence on the human body; and, articles, falling within the range of agents used to sterilize, kill insects and for similar purposes. All of the articles exclude those intended at the same time to be prescribed to diagnose, cure, alleviate, treat or prevent diseases in humans or animals, and for pharmaceutically affecting the structure and function of humans or animals.

When used as a quasi-drug additive, the composition of the present invention may be suitably used as it is, or in combination with another quasi-drug or quasi-drug component using a typical method. The amount of the active ingredient in the mixture may be properly determined depending on the purpose of use.

Examples of the quasi-drug to which the composition of the present invention may be applied include, but are not limited to, disinfectants, shower foams, mouthwash, wet tissues, detergent soap, handwashing materials, humidifier fillers, masks, ointments, and a filter coating.

In accordance with a further aspect thereof, the present invention provides a health functional food composition for preventing or improving inflammation, comprising the mixture of extracts from *Trachelospermi Caulis* and *Paeonia*

*Suffruticosa* Andrews as an active ingredient. As for the mixture of extracts from *Trachelospermi Caulis* and *Paeonia Suffruticosa* Andrews, its description was given above. In greater detail, the composition of the present invention may be added to a health functional food composition to be used to prevent or improve inflammation.

When used as a health functional food additive, the extract mixture of the present invention may be suitably used in unchanged form, or in a combination with another health functional food or health functional food component made using a typical method. The amount of the active ingredient may be properly determined depending on the purpose of use.

There is no particular limitation on the kind of health functional food to which the extract mixture of the present invention can be added. Examples of such health functional food include meats, sausages, breads, chocolates, candies, snacks, confectionery, pizzas, ramen noodles, other noodles, gums, dairy products such as ice-creams, various soups, beverages, teas, drinks, alcoholic beverages, and vitamin complexes. All typically accepted health functional foods may contain the active ingredient according to the present invention. Also, animal feeds fall within the scope of the present invention.

In addition, the health functional food composition of the present invention may comprise various nutrients, vitamins, minerals, electrolytes, flavors, colorants, pectic acid and salts thereof, alginic acid and salts thereof, organic acids, protective colloidal thickeners, pH modifiers, stabilizers, antiseptics, glycerin, alcohols, and carbonating agents used in carbonated beverages. Moreover, the composition of the present invention can contain the fruit flesh used to prepare natural fruit juices, fruit beverages and vegetable beverages.

In accordance with still a further aspect thereof, the present invention provides a cosmetic composition for preventing or improving inflammation, comprising the mixture of extracts from *Trachelospermi Caulis* and *Paeonia Suffruticosa* Andrews as an active ingredient. As for the mixture of extracts from *Trachelospermi Caulis* and *Paeonia Suffruticosa* Andrews, its description was given above. In greater detail, the composition of the present invention may be added to a cosmetic composition to be used to prevent or improve inflammation.

The cosmetic composition of the present invention may be formulated into a general emulsion or water-soluble form. Examples of the emulsion cosmetics include nutrition lotions, creams, essences and the like. A skin lotion is a kind of the water-soluble cosmetic forms. Examples of the suitable cosmetic forms include, but are not limited to, solutions, gels, solid or paste preparations, oil-in-water emulsions, suspensions, microemulsions, microcapsules, microgranules or ionic liposomes, non-ionic vesicle dispersions, creams, skins, lotions, powders, ointments, sprays, conceal sticks, etc. Also, it may be prepared into a foam form or an aerosol form having a quantity of compressed propellant.

In addition, the cosmetic composition may comprise lipids, organic solvents, dissolving agents, thickening agents, gelling agents, softeners, anti-oxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, and/or other general supplements used in the science field related to skin.

In accordance with another aspect thereof, the present invention provides a method for preparing a pharmaceutical composition for preventing or treating an inflammatory disease, comprising (a) extracting *Trachelospermi Caulis* in an aqueous ethanol solution, followed by filtering to separate filtrate and remnant, and drying the filtrate to obtain an extract containing arctigenin in an amount of from 0.05 to 1.5 wt %, the arctigenin serving as an index substance for *Trachelospermi Caulis*; (b) extracting *Paeonia Suffruticosa* Andrews in an aqueous ethanol solution, followed by filtering to separate filtrate and remnant, and drying the filtrate to obtain an extract containing paeoniflorin in an amount of from 1.8 to 5.3 wt %, the paeoniflorin serving as an index substance for *Paeonia Suffruticosa* Andrews; and (c) mixing the *Trachelospermi Caulis* extract of step (a) and the *Paeonia Suffruticosa* Andrews extract of step (b) at a ratio of 1:1 to 3:1, based on dry weight to obtain a mixture.

In steps (a) and (b), *Trachelospermi Caulis* and *Paeonia Suffruticosa* Andrews are extracted with an ethanol solution, followed by filtering to separate filtrate and remnant, and drying the filtrate to obtain extracts containing arctigenin in an amount of from 0.05 to 1.5 wt % and paeoniflorin in an amount of from 1.8 to 5.3 wt %, respectively. The steps (a) and (b) may be conducted in the order, in a reverse order or concurrently.

The *Trachelospermi Caulis* extract and the *Paeonia Suffruticosa* Andrews extract may be in the form of a solid extract or a soft extract, with preference for a soft extract. As for the solid extract and the soft extract, their descriptions are as given above.

In one embodiment of the present invention, herbal materials of *Trachelospermi Caulis* and *Paeonia Suffruticosa* Andrews that meet the requirement of the Korean Pharamacopoeia were cut, washed, extracted with 95% ethanol, and filtered, and the filtrates were pooled, concentrated, dried and pulverized to obtain solid extracts of *Trachelospermi Caulis* and *Paeonia Suffruticosa* Andrews (FIG. 1). Herbal materials of *Trachelospermi Caulis* and *Paeonia Suffruticosa* Andrews were washed, extracted with 95% ethanol, and filtered, and the filtrates were pooled and concentrated to obtain soft extracts of *Trachelospermi Caulis* and *Paeonia Suffruticosa* Andrews (FIG. 2).

In step (c), the *Trachelospermi Caulis* extract of step (a) and the *Paeonia Suffruticosa* Andrews extract of step (b) are mixed at a ratio of from 1:1 to 3:1, based on dry weight to obtain a mixture. In this mixture, the *Trachelospermi Caulis* extract and the *Paeonia Suffruticosa* Andrews extract do not interfere with nor disturb their respective activities, but exhibit a mutual complementary medicinal mechanism, and thus can be used for preparing the effective pharmaceutical composition. As for the pharmaceutical composition, its description is as given above.

The inflammatory disease, as elucidated above, preferably includes edema, dermatitis, allergy, atopy, asthma, conjunctivitis, peridontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatoid arthritis, periarthritis of the shoulder, tendonitis, tenosynovitis, myositis, hepatitis, cystitis, nephritis, sjogren's syndrome and multiple sclerosis, with a preference for rheumatoid arthritis and edema, the former being more strongly preferred.

The method of the present invention may further comprise (d) combining the mixture of step (c) with silicon dioxide and ethanol; and (e) drying the combination of step (d) by completely evaporating the ethanol to obtain a dry mixture for use in oral dosage formulations.

In step (d), the mixture of step (c) is combined with silicon dioxide, followed by the addition of ethanol thereto. This step is intended to suppress the hygroscopicity of the mixture. In detail, the mixture of the *Trachelospermi Caulis* extract and the *Paeonia Suffruticosa* Andrews is combined with silicon dioxide using a high-speed mixer, and then ethanol is added thereto. Silicon dioxide may be added before or after the *Trachelospermi Caulis* extract and the *Paeonia Suffruticosa* Andrews extract are mixed together.

In this method, silicon dioxide may be used in an amount of from 30 to 100 weight parts, based on 100 weight parts of the mixture of step (c). With regard to the weight ratio, its description is as given above.

Also, a pharmaceutically acceptable excipient may be added to the mixture of the *Trachelospermi Caulis* extract and the *Paeonia Suffruticosa* Andrews extract. The excipient may include, but is not limited to, microcrystalline cellulose or potassium silicate. Microcrystalline cellulose or potassium silicate may be used in an amount of from 10 to 50 weight parts, based on 100 weight parts of the mixture of the *Trachelospermi Caulis* extract plus the *Paeonia Suffruticosa* Andrews extract.

In step (e), the combination of step (d) is dried by completely evaporating the ethanol to obtain a dry mixture for use in an oral dosage formulation resistant to moisture. The evaporation of ethanol is preferably conducted in a vacuum or using a hot-air dryer, the latter being preferred. After step (e), a typical additional process apparent to those skilled in the art may be used to formulate the combination into various forms including powders, granules, fillers, hard capsules, tablets or suspensions, etc. The tablets are highly stable not only because the combination itself is resistant to moisture, but also because when the combination is formulated thereinto, the tablets themselves have anti-hygroscopic effects.

In accordance with still another aspect thereof, the present invention provides a method of treating an inflammatory disease, comprising administering the pharmaceutical composition to a subject suspected of having the inflammatory disease.

The term "subject suspected of having an inflammatory disease," as used herein, means an animal including a human, which has been attacked with or is apt to be attacked by an inflammatory disease. An inflammatory disease may be cured by administering the pharmaceutical composition comprising a mixture of the *Trachelospermi Caulis* and *Paeonia Suffruticosa* Andrews extracts of the present invention to a subject suspected of having the inflammatory disease. As for the inflammatory disease, its description was as given above.

The term "administration," as used herein, is intended to refer to introduction of the pharmaceutical composition of the present invention into a subject suspected of an having inflammatory disease in a suitable manner. So long as it allows the compound of the present invention to reach a target tissue, any route of administration, whether oral or parenteral, may be used.

The treatment method of the present invention includes administering a pharmaceutically effective amount of the pharmaceutical composition comprising the extracts from *Trachelospermi Caulis* and *Paeonia Suffruticosa* Andrews. It will be apparent to those skilled in the art that the suitable total daily dose may be determined by an attending physician within the scope of sound medical judgment. Also, the composition may be administered in a single dose or it may be spread out over multiple doses per day. For purposes of the present invention, however, the therapeutically effective dose for a certain patient depends on various factors including the kind and extent of the response sought to be achieved, the use of any other agents according to the intended use, patient's age, weight, general health state, sex and diet, the time of administration, the route of administration, the rate of excretion of the composition, the duration of the treatment, other drugs mixed with or concurrently administered together with the composition, and other factors well known in the medical art.

Mode for the Invention

A better understanding of the present invention may be obtained through the following examples which are set forth to illustrate, but are not to be construed as limiting the present invention.

PREPARATION EXAMPLE 1: Preparation of Pharmaceutical Formulations of *Trachelospermi Caulis* and *Paeonia Suffruticosa* Andrews 1-1. Preparation of 95% Ethanol Solid Extract of *Trachelospermi Caulis* and *Paeonia Suffruticosa* Andrews Herbal materials (*Trachelospermi Caulis* and *Paeonia Suffruticosa* Andrews) which met the requirement of the Korean Pharmacopoeia were cut and weighed. They were extracted with 95% ethanol, and heated to exude active ingredients. The exudate was filtered and the filtrates were pooled and concentrated. To the concentrate was added 95% ethanol, followed by letting it stand for 24 hours and then filtering. The filtrate was concentrated at a reduced pressure and dried in a vacuum to afford respective solid extracts from *Trachelospermi Caulis* and *Paeonia Suffruticosa* Andrews (FIG. 1). The concentration ratio of the solid extract was approximately 40:1.

After the ethanol extraction was conducted in the same manner, the extracts were concentrated at reduced pressure and dried in a vacuum to afford solid extracts. The concentration ratio was approximately 20:1.

1-2. Preparation of 95% Ethanol Soft Extract of *Trachelospermi Caulis* and *Paeonia Suffruticosa* Andrews Selected materials (*Trachelospermi Caulis* and *Paeonia Suffruticosa* Andrews) were weighed, and heated in 95% ethanol twice. The resulting exudate was filtered and the filtrate was concentrated at a reduced pressure to afford respective soft extracts from *Trachelospermi Caulis* and *Paeonia Suffruticosa* Andrews (FIG. 2). The concentration ratio of the soft extract was approximately 20:1.

PREPARATION EXAMPLE 2: Preparation of Mixture Extract

The herbal materials of *Trachelospermi Caulis* and *Paeonia Suffruticosa* Andrews were mixed in equal amounts and the mixture was extracted with 95% ethanol in the same manner as in Preparation Example 1 to obtain a solid extract and a soft extract.

PREPARATION EXAMPLE 3: Preparation of Extract Mixture

The solid extracts from *Trachelospermi Caulis* and *Paeonia Suffruticosa* Andrews, having the same concentration ratio, prepared in Preparation Example 1, were mixed together at a weight ratio of 1:1 to obtain a solid extract mixture.

Likewise, the soft extracts from *Trachelospermi Caulis* and *Paeonia Suffruticosa* Andrews, having the same concentration ratio, prepared in Preparation Example 1, were mixed together at a weight ratio of 1:1 to obtain a soft extract mixture.

PREPARATION EXAMPLE 4: Preparation of Dry Granules from *Trachelospermi Caulis* and *Paeonia Suffruticosa* Andrews Extracts The soft extracts from *Trachelospermi Caulis* and *Paeonia Suffruticosa* Andrews, obtained in Preparation Example 1-2, were respectively filtered by precipitation in 50% ethanol and the ethanol solvent was recovered and concentrated. After drying in a vacuum, the concentrate was pulverized to obtain dry granules of *Trachelospermi Caulis* and *Paeonia Suffruticosa* Andrews, respectively.

PREPARATION EXAMPLE 5: Preparation of Dry Mixed Granules of *Trachelospermi Caulis* and *Paeonia Suffruticosa* Andrews Containing Microcrystalline Cellulose Each of the soft extracts of *Trachelospermi Caulis* and *Paeonia Suffruticosa* Andrews, obtained in Preparation Example 1-2, was dissolved in an amount of 5 g in 50 mL of 95% ethanol to obtain respective ethanol solutions of *Trachelospermi Caulis* and *Paeonia Suffruticosa* Andrews. To each of the ethanol solutions of *Trachelospermi Caulis* and *Paeonia Suffruticosa* Andrews was added 2.5 g of microcrystalline cellulose, after which ethanol was added thereto with slow stirring. After homogeneously mixing, the ethanol was completely evaporated using a hot-air dryer to obtain *Trachelospermi Caulis* dry mixed granules and *Paeonia Suffruticosa* Andrews dry mixed granules (1), both containing microcrystalline cellulose.

In addition, *Trachelospermi Caulis* dry mixed granules and *Paeonia Suffruticosa* Andrews dry mixed granules (2) were prepared in the same manner, with the exception that 10 g of microcrystalline cellulose was added to each of the ethanol solutions of *Trachelospermi Caulis* and *Paeonia Suffruticosa* Andrews.

PREPARATION EXAMPLE 6: Preparation of Dry Mixed Granules of *Trachelospermi Caulis* and *Paeonia Suffruticosa* Andrews Containing Silicon Dioxide Each of the soft extracts from *Trachelospermi Caulis* and *Paeonia Suffruticosa* Andrews, obtained in Preparation Example 1-2, was dissolved in an amount of 5 g in 50 mL of 95% ethanol to obtain respective ethanol solutions of *Trachelospermi Caulis* and *Paeonia Suffruticosa* Andrews. To each of the ethanol solutions of *Trachelospermi Caulis* and *Paeonia Suffruticosa* Andrews was added 2.5 g of silicon dioxide, after which ethanol was added thereto with slow stirring. After homogeneously mixing, the ethanol was completely evaporated using a hot-air dryer to obtain *Trachelospermi Caulis* dry mixed granules and *Paeonia Suffruticosa* Andrews dry mixed granules, both containing silicon dioxide.

PREPARATION EXAMPLE 7: Preparation of Dry Mixed Granules Containing Corn Starch

Each of the soft extracts of *Trachelospermi Caulis* and *Paeonia Suffruticosa* Andrews, obtained in Preparation Example 1-2, was dissolved in an amount of 5 g in 50 mL of 95% ethanol to obtain respective ethanol solutions of *Trachelospermi Caulis* and *Paeonia Suffruticosa* Andrews. To each of the ethanol solutions of *Trachelospermi Caulis* and *Paeonia Suffruticosa* Andrews was added 15 g of corn starch, after which ethanol was added thereto with slow stirring. After homogeneously mixing, the ethanol was completely evaporated using a hot-air dryer to obtain *Trachelospermi Caulis* dry mixed granules and *Paeonia Suffruticosa* Andrews dry mixed granules, both containing corn starch.

EXAMPLE 1: Analysis of Content of Index Substance

The solid extract and the soft extract obtained in Preparation Example were analyzed for the contents of index substances using high performance liquid chromatography (HPLC) under the following conditions.

1-1. Analysis for Index Substance for 95% Ethanol Extract of *Trachelospermi Caulis*

Arctigenin of the following Chemical Formula 1, an index substance for the *Trachelospermi Caulis* extract prepared in Preparation Example 1, was quantitatively measured using high-performance liquid chromatography.

(1) Index Substance for *Trachelospermi Caulis*: Arctigenin (Chemical Formula 1)

[Chemical Formula 1]

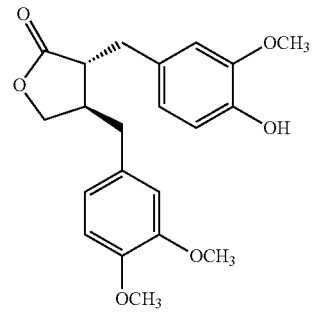

(2) Analysis Condition of Arctigenin
Column: Waters X-bridge C18 (250*4.6 mm/5 μm)
Injection volumn: 20 μL
Flow rate: 1 ml/min
Detection wavelength: UV 230 nm
Mobile solvent: purified water, ACN
Analysis condition of mobile solvent

TABLE 2

| Min | Purified Water | ACN |
|---|---|---|
| 0 | 80 | 20 |
| 30 | 60 | 40 |
| 35 | 80 | 20 |
| 40 | 80 | 20 |

Figure 3:
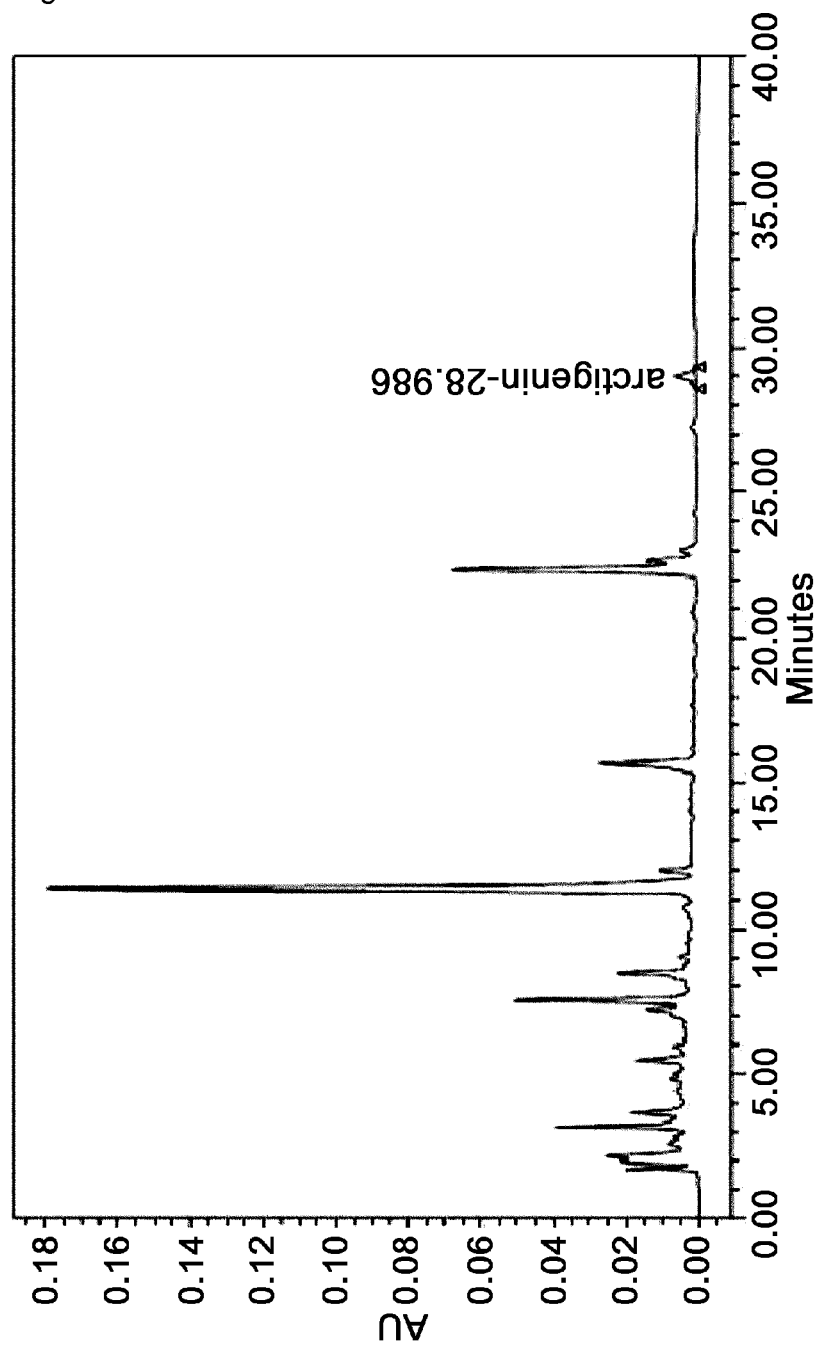
FIG. 3 is an HPLC chromatogram of a 95% ethanol extract from *Trachelospermi Caulis*.

(3) Arctigenin HPLC Chromatogram
Peaks of Arctigenin were read from the chromatogram as shown in FIG. 3.

1-2. Analysis for Index Substance for 95% Ethanol Extract of *Paeonia Suffruticosa* Andrews Paeoniflorin of the following Chemical Formula 2, an index substance for the *Paeonia Suffruticosa* Andrews extract prepared in Preparation Example 1, was quantitatively measured using high-performance liquid chromatography.

(1) Index Substance for *Paeonia Suffruticosa* Andrews: Paeoniflorin (Chemical Formula 2)

[Chemical Formula 2]

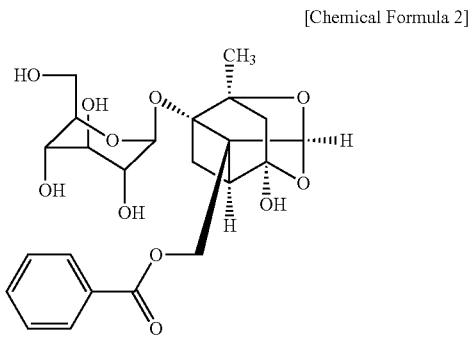 [SMILES: C[C@@]12C[C@@]3(O)O[C@H](O1)[C@]1(COC(=O)c4ccccc4)[C@@H]3C[C@]12OC1OC(CO)C(O)C(O)C1O]

(2) Analysis Condition of Paeoniflorin
Column: Waters X-bridge C18 (250*4.6 mm/5 μm)
Injection volumn): 20 μL
Flow rate: 1 ml/min
Detection wavelength: UV 230 nm
Mobile solvent: 0.1% phosphate, ACN
Analysis condition of mobile solvent

TABLE 3

| Min | 0.1% Phosphate | ACN |
| --- | --- | --- |
| 0 | 89 | 11 |
| 25 | 89 | 11 |
| 30 | 30 | 70 |
| 35 | 30 | 70 |
| 40 | 89 | 11 |
| 45 | 89 | 11 |

Figure 4:
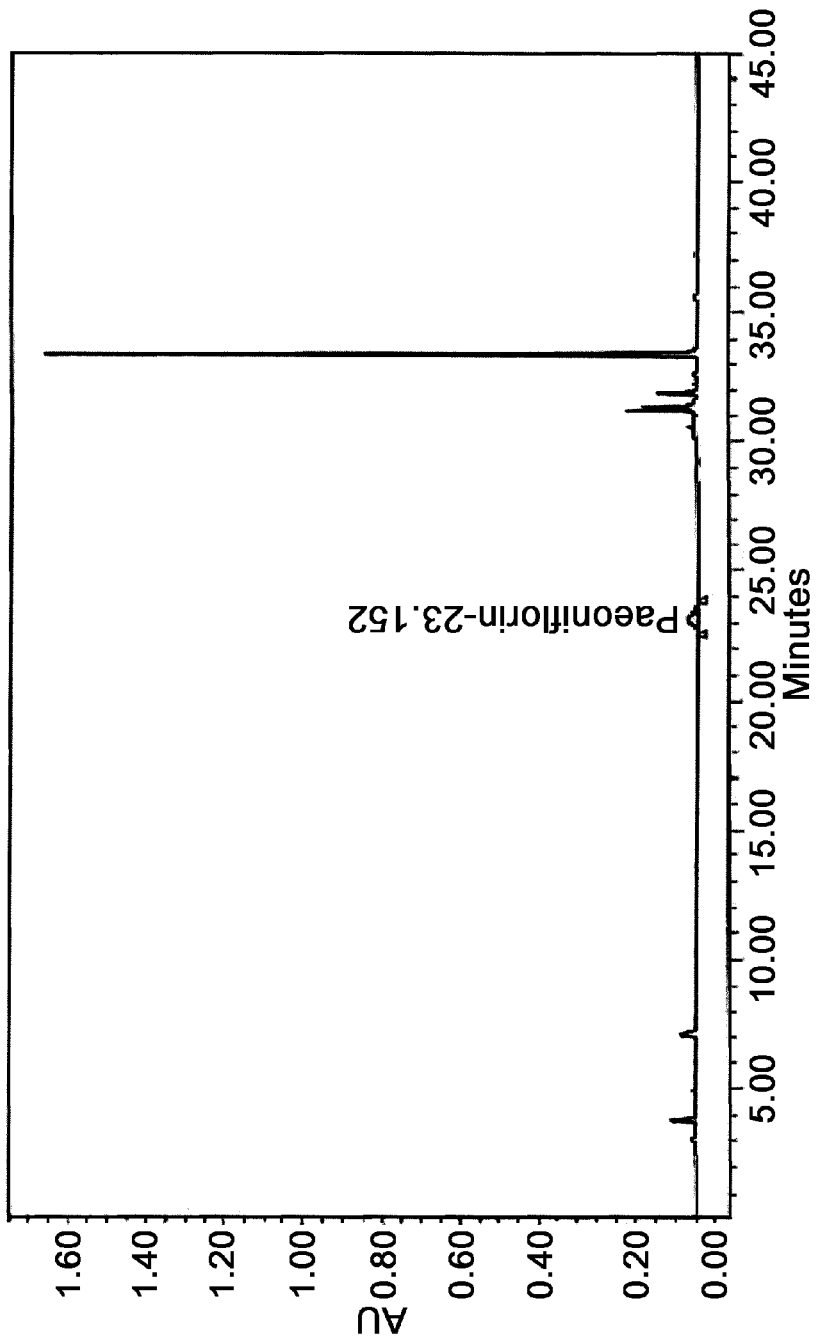
FIG. 4 is an HPLC chromatogram of a 95% ethanol extract from *Paeonia Suffruticosa* Andrews.

(3) Paeoniflorin HPLC Chromatogram
Peaks of paeoniflorin were read from the chromatogram as shown in FIG. 4.

1-3. Analysis for Index Substance for 95% Ethanol Extract Mixture of *Trachelospermi Caulis* and *Paeonia Suffruticosa* Andrews The extract mixture obtained in Preparation Example 3 was analyzed for the contents of the index substances Arctigenin and paeoniflorin using HPLC in the same manner as described above.

Peaks of arctigenin (a) and paeoniflorin (b) were read off the chromatograms of FIG. 5, showing patterns similar to those of respective index substances for *Trachelospermi Caulis* and *Paeonia Suffruticosa* Andrews. These results indicate that the analysis for index substances is suitable because peaks of the two index substances do not overlap nor interfere with each other, showing specificity, and reproductivity of contents.

EXAMPLE 2: Analysis for Contents of Index Substances in Solid Extract and Soft Extract According to Concentration Ratio The *Trachelospermi Caulis* extract and the *Paeonia Suffruticosa* Andrews extract were analyzed for the content of the index substances Arctigenin and paeoniflorin according to concentration ratio under the same condition as in Example 1. The content of the index substance arctigenin in the *Trachelospermi Caulis* was measured to range from 0.05 to 1.5 wt % while the *Paeonia Suffruticosa* Andrews extract contained the index substance paeoniflorin in an amount of from 1.8 to 5.3 wt % (Table 4). In Table 4, Rot No. shows herbal materials different in gathering site and time.

TABLE 4

| Herb | Property | Rot. No. | Content (%) | Concentration Ratio |
| --- | --- | --- | --- | --- |
| Trachelospermi Caulis | solid extract | 1(Hebei Sheng) | 0.1 | ×40 |
| | | 2(Hebei Sheng) | 1.5 | ×40 |
| | | 3(Hebei Sheng) | 0.11 | ×10 |
| | | 4(Hebei Sheng) | 0.05 | ×8 |
| | soft extract | 5(Henan Sheng) | 0.2 | ×40 |
| | | 6(Anhui Sheng) | 0.21 | ×20 |
| | | 7(Henan Sheng) | 0.2 | ×20 |
| Paeonia Suffruticosa Andrews | solid extract | 8(Dongbei San Sheng) | 5.3 | ×14.3 |
| | | 9(Dongbei San Sheng) | 3.2 | ×15 |
| | | 10(Dongbei San Sheng) | 2.8 | ×10 |
| | | 11(Dongbei San Sheng) | 4.8 | ×16.5 |
| | | 12(Dongbei San Sheng) | 3.8 | ×16.5 |
| | soft extract | 13(Henan Sheng) | 1.8 | ×20 |
| | | 14(Anhui Sheng) | 2.7 | ×13 |
| | | 15(Henan Sheng) | 2.93 | ×20 |
| | | 16(Anhui Sheng) | 3.3 | ×20 |

EXAMPLE 3: Assay of *Trachelospermi Caulis* and *Paeonia Suffruticosa* Andrews Extract Mixture for Inhibitory Activity Against Nitric Oxide and Cytokine To examine the anti-inflammatory activity of the extract mixture of the present invention, the extract mixture was assayed for inhibitory activity against nitric oxide and cytokine within cells. All measurements were expressed as percentages of the control treated with LPS only. For comparison, Joins tablet, a conventional tablet medication for arthritis, and the composite herbal medicine of Korean Patent No. 10-0847740 (SI-00413) issued to the present inventors were used.

3-1. Cell Preparation

Mouse macrophage RAW 264.7 (ATCC, #TIB-71) was maintained at 37° C. in DMEM (Dulbecco's Modified Eagle Medium supplemented with 10% FBS (fetal bovine serum), penicillin (100 units/mL) and streptomycin sulfate (100 μg/mL) under a 5% $CO_2$ condition.

3-2. Measurement of Inhibitory Activity of Extract Mixture Against Nitric Oxide (NO)

The mouse-derived macrophage RAW 264.7 was used to assay inhibitory activity against nitric oxide. The level of nitric oxide in the medium was determined using an ELISA assay kit (Promega, G2930). For this, $OD_{550\,nm}$ UV was read on a microplate reader. In this regard, the cells were treated with predetermined concentrations of the specimens at which no cytotoxicity was developed.

As seen in FIG. 6, the production of NO was inhibited by 92.8% by the *Trachelospermi Caulis* extract (100 μg/mL), 80.3% by the *Paeonia Suffruticosa* Andrews extract (100

μg/mL) and 91.3% by the mixture of extracts from *Trachelospermi Caulis* and *Paeonia Suffruticosa* Andrews (100 μg/mL). They were found to inhibit the production of nitric oxide at higher yield than did the Joins tablet. The inhibitory activity against nitric oxide of the extract mixture was measured to be similar to that of individual extracts even when the extract mixture was used at half of the concentration of individual extracts. Thus, the extract mixture acts as an excellent anti-inflammatory composite agent in which the individual extracts are mutually complementary without interfering or obstructing their own activities because the individual extracts, when used in combination, were identified to have a synergistically inhibitory effect on the production of nitric oxide.

3-3. Measurement of Inhibitory Activity of Extract Mixture Against IL-6

The mouse-derived macrophage RAW 264.7 was used to assay inhibitory activity against IL-6. The level of IL-6 in the medium was determined using an ELISA assay kit (Thermo, EM2IL6). For this, $OD_{450\ nm}$ and $OD_{550\ nm}$ UV were read on a microplate reader. In this regard, the cells were treated with predetermined concentrations of the specimens at which no cytotoxicity was developed.

As seen in FIG. 6, the production of IL-6 was inhibited by 70.9% by the *Trachelospermi Caulis* extract (100 μg/mL), 82.7% by the *Paeonia Suffruticosa* Andrews extract (100 μg/mL) and 76.7% by the mixture of extracts from *Trachelospermi Caulis* and *Paeonia Suffruticosa* Andrews (100 μg/mL). Effectively inhibiting the release of IL-6, the extracts were anticipated to have high therapeutic activity for inflammation. The inhibitory activity against IL-6 of the extract mixture was measured to be similar to that of individual extracts even when the extract mixture was used at half of the concentration of individual extracts. Thus, the extract mixture acts as an excellent anti-inflammatory composite agent in which the individual extracts are mutually complementary without interfering or obstructing their own activities because the individual extracts, when used in combination, were identified to have a synergistically inhibitory effect on the production of IL-6.

3-4. Measurement of Inhibitory Activity of Extract Mixture against IL-1β

The mouse-derived macrophage RAW 264.7 was used to assay inhibitory activity against IL-1β. The level of IL-1β in the medium was determined using an ELISA assay kit (Thermo, EM2IL1b). For this, $OD_{450\ nm}$ and $OD_{550\ nm}$ UV were read on a microplate reader. In this regard, the cells were treated with predetermined concentrations of the specimens at which no cytotoxicity was developed.

As seen in FIG. 6, the production of IL-1β was inhibited by 77.3% by the *Trachelospermi Caulis* extract (100 μg/mL), 59.4% by the *Paeonia Suffruticosa* Andrews extract (100 μg/mL) and 86.5% by the mixture of extracts from *Trachelospermi Caulis* and *Paeonia Suffruticosa* Andrews (100 μg/mL). Effectively inhibiting the release of IL-1β at higher yield than did the Joins tablet, the extracts were anticipated to have high therapeutic activity for inflammation. The inhibitory activity against IL-1β of the extract mixture was measured to be synergistic to that of individual extracts even when the extract mixture was used at a half of the concentration of individual extracts. Thus, the extract mixture acts as an excellent anti-inflammatory composite agent in which the individual extracts are mutually complementary without interfering or obstructing their own activities because the individual extracts, when used in combination, were identified to have a synergistically inhibitory effect on the production of T IL-1β.

3-5. Measurement of Inhibitory Activity of Extract Mixture against Nitric Acid and IL-1β According to Concentration of the Mixture The cells were treated with 200 ng/ml of LPS, or 100, 30, 10, 3, or 1 μg/mL of the mixture of extracts from *Trachelospermi Caulis* and *Paeonia Suffruticosa* Andrews before conducting assay for NO and IL-1β in the same manner as described above, with the exception that an ELISA assay kit (R&D systems, MLBOOB) was used for IL-1β.

Figure 7:
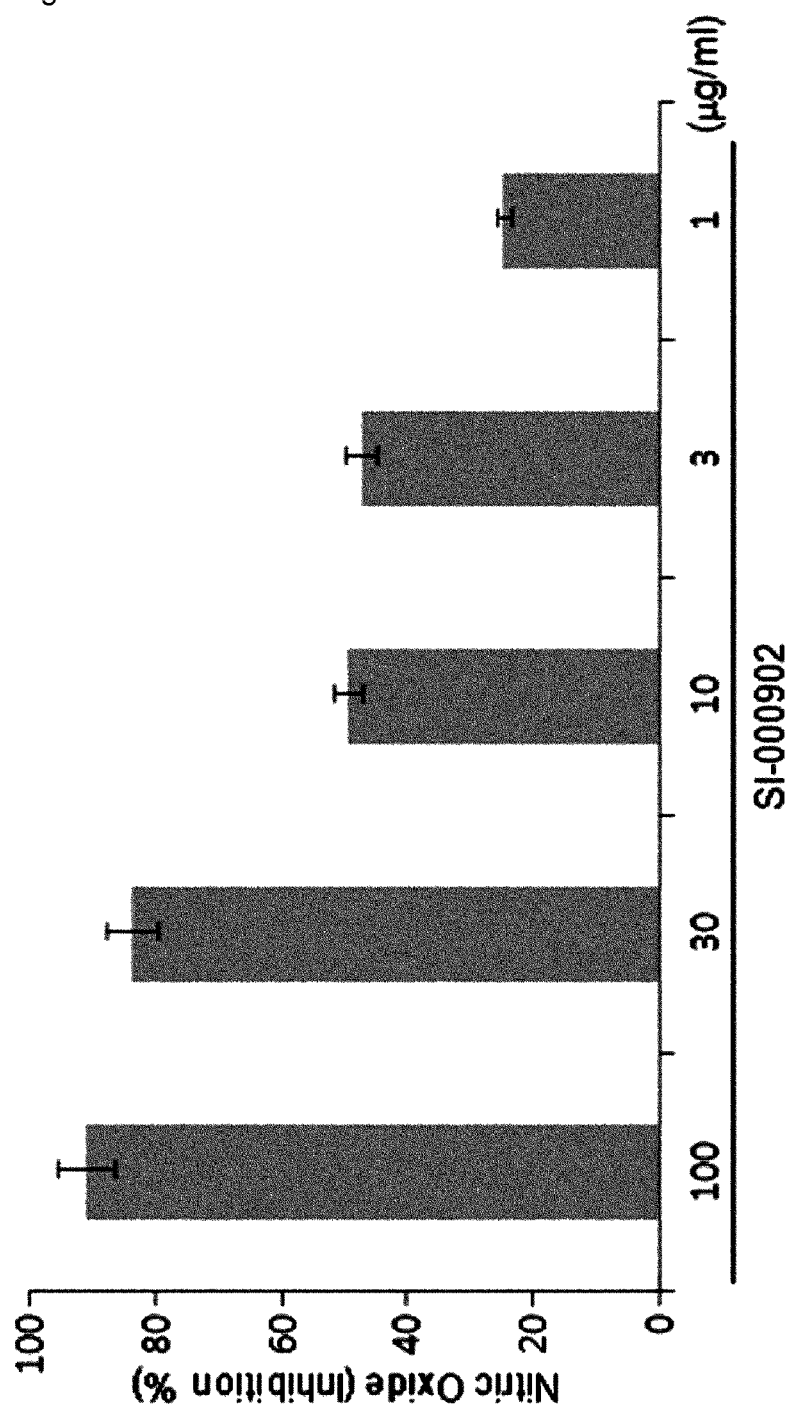
FIG. 7 is a graph showing the inhibitory activity of a mixture of extracts from *Trachelospermi Caulis* and *Paeonia Suffruticosa* Andrews (SI-000902) against the release of nitric oxide (NO) when the mixture is applied at various concentrations to mouse-derived macrophage RAW 264.7.
Figure 8:
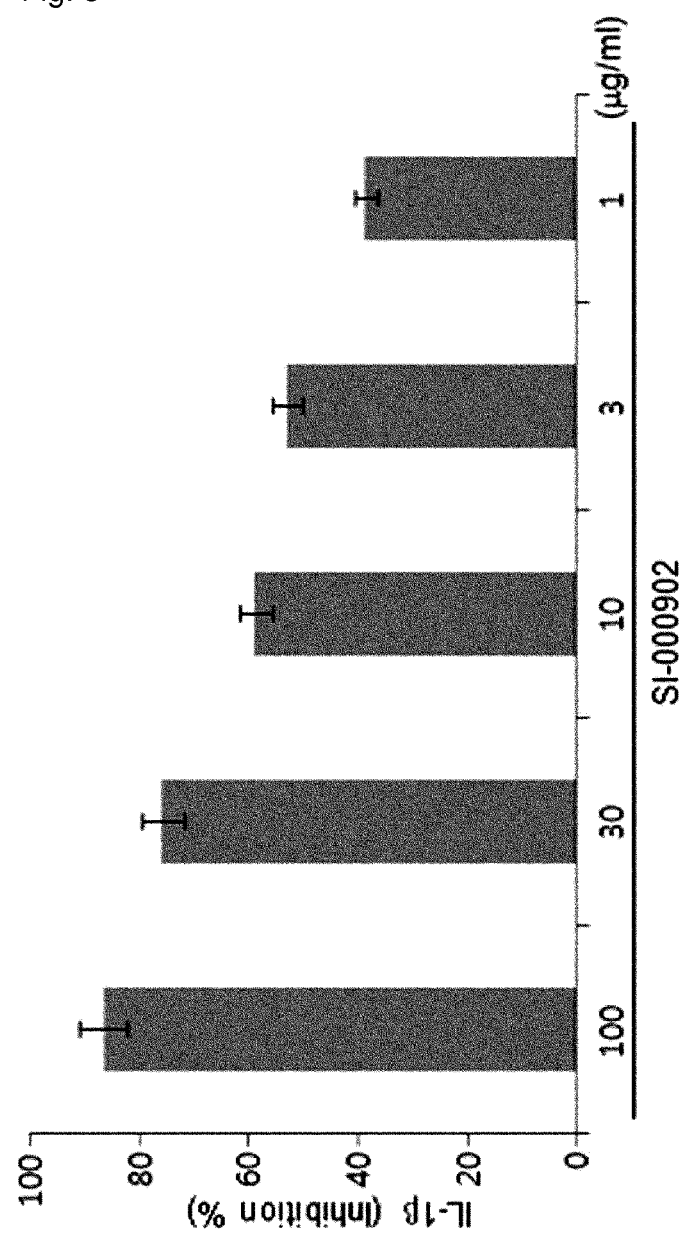
FIG. 8 is a graph showing the inhibitory activity of a mixture of extracts from *Trachelospermi Caulis* and *Paeonia Suffruticosa* Andrews (SI-000902) against the release of IL-1β when the mixture is applied at various concentrations to mouse-derived macrophage RAW 264.7.

As can be seen in FIGS. 7 and 8, the extract mixture inhibited the release of nitric oxide and IL-1β in a dose-dependent manner.

These assays in mouse-derived macrophage RAW 264.7 demonstrate that the mixture of extracts from *Trachelospermi Caulis* and *Paeonia Suffruticosa* Andrews can form an excellent anti-inflammatory composite agent in which the individual extracts are mutually complementary without interfering or obstructing their own activities because the individual extracts, when used in combination, were identified to have a synergistically inhibitory effect on the production of nitric oxide (NO), IL-6 and IL-1β.

EXAMPLE 4: Assay of the Mixture of Extracts *Trachelospermi Caulis* and *Paeonia Suffruticosa* Andrews for Inhibitory Activity Against IL-6-Induced Signaling Pathway 4-1. Assay for Inhibitory Activity Against IL-6-Induced STAT3 Phosphorylation HepG2 cells were plated at a density of $5 \times 10^4$ cells/well in 6-well plates and grown to 80% confluency. After the medium was exchanged with a serum-free medium, the cells were further cultured for 6 hours and treated for 30 min with the *Trachelospermi Caulis* extract, the *Paeonia Suffruticosa* Andrews extract, and the mixture of extracts from *Trachelospermi Caulis* and *Paeonia Suffruticosa* Andrews.

Thereafter, the cells were incubated for 10 min with 20 ng/ml IL-6, followed by cell lysis in 40 μL of lysis buffer [pH 8, 20 mM Tris-HCl, 137 mM NaCl, 10% glycerol, 1% Triton X-100, 1 mM $Na_3VO_4$, 2 mM EDTA, 1 mM PMSF, 20 mM leupeptin, 20 μg/ml aprotonin, Sigma]. After centrifugation (13,000 g, 15 min), proteins were obtained in the supernatant. HepG2 cells treated without the samples IL-6 were used as a control. The proteins were quantitatively analyzed using a DC protein assay kit (Bio-Rad, USA). The proteins were loaded to 10% SDS polyacrylamide gel (SDS-PAGE) and separated by electrophoresis at 30 mA for 2 hours. Then, they were transferred from the gel to a PVDF membrane (Weatran S, pore size 0.2; Whatman, USA) at 90 V for 90 min. The membrane was blocked for 4 to 12 hours with Tris-buffer (T-TBS; 50 mM Tri-HCl, pH 7.6, 150 mM NaCl, 0.2% Tween-20, 5% skim milk; Sigma) and washed five times with T-TBS. The membrane was treated for 2 hours with anti-phosphorylated-STAT3 polyclonal antibodies (1:1000 diluted) as a primary antibody and washed five times with T-TBS before incubation for 1 hour with HRP-conjugated, anti-rabbit antibody (1:5000 diluted) as a secondary antibody. After washing with T-TBS, the film was developed with an ECL kit (Amersham, USA) in a dark room.

As can be seen in FIG. 9, phosphorylated STAT3 was detected at lower levels in the group treated with the mixture of extracts from *Trachelospermi Caulis* and *Paeonia Suffruticosa* Andrews than the control and also than the groups treated with the *Trachelospermi Caulis* extract or the *Paeonia Suffruticosa* Andrews extract. Thus, the extract mixture was observed to inhibit IL-6-induced STAT3 phosphorylation. Consequently, the mixture of extracts from *Trachelospermi Caulis* and *Paeonia Suffruticosa* Andrews according to the present invention has the function of suppressing the release of IL-6 and thus inhibiting the IL-6-induced signaling pathway.

4-2. Assay for Inhibitory Activity Against PMA-Induced ERK Phosphorylation

To examine whether the inhibitory activity of the mixture of extracts from *Trachelospermi Caulis* and *Paeonia Suffruticosa* Andrews, revealed in Example 4-1, is selective for IL-6-induced signaling pathway or not, the extract mixture was assayed for inhibitory activity against PMA-induced ERK phosphorylation, which is different from IL-6-induced signaling pathway.

HepG2 cells were treated with 20 ng/ml PMA in the same manner as in the assay for IL-6-induced STAT3 phosphorylation while HepG2 cells treated without the samples and PMA were used as a control.

As shown in FIG. 9, no inhibitory effects were detected on PMA-induced ERK phosphorylation. Therefore, the mixture of extracts from *Trachelospermi Caulis* and *Paeonia Suffruticosa* Andrews cannot inhibit PMA-induced signaling pathway, but its inhibitory activity is specific for IL-6-induced signaling pathway.

4-3. Assay for Inhibitory Activity Against IL-6-Induced JAK2 and gp130 Phosphorylation HepG2 cells were plated at a density of $5 \times 10^4$ cells/well in 6-well plates and grown to 80% confluency. After the medium was exchanged with a serum-free medium, the cells were further cultured for 6 hours and treated for 30 min with the *Trachelospermi Caulis* extract, the *Paeonia Suffruticosa* Andrews extract, and the mixture of extracts from *Trachelospermi Caulis* and *Paeonia Suffruticosa* Andrews.

Thereafter, the cells were incubated for 10 min with 20 ng/ml IL-6, followed by cell lysis in 40 μL of lysis buffer [pH 8, 20 mM Tris-HCl, 137 mM NaCl, 10% glycerol, 1% Triton X-100, 1 mM $Na_3VO_4$, 2 mM EDTA, 1 mM PMSF, 20 mM leupeptin, 20 μg/ml aprotonin, Sigma, USA]. After centrifugation (13,000 g, 15 min), proteins were obtained in the supernatant. The supernatant was incubated for 4 to 12 hours with anti-JAK2 antibodies and anti-gp130 antibodies (Cell signaling, INC.), followed by immunoprecipitation with protein A/G plus agarose (Santa Cruz Biotechnology, USA). After centrifugation, the precipitate was washed three times with buffer and used as a sample for electrophoresis. HepG2 cells treated without the samples IL-6 were used as a control. The proteins were quantitatively analyzed using a DC protein assay kit (Bio-Rad, USA). The proteins were loaded to 8% SDS polyacrylamide gel (SDS-PAGE) and separated by electrophoresis at 30 mA for 2 hours. Then, they were transferred from the gel to a PVDF membrane (Weatran S, pore size 0.2; Whatman, USA) at 90 V for 90 min. The membrane was blocked for 4 to 12 hours with Tris-buffer (T-TBS; 50 mM Tri-HCl, pH 7.6, 150 mM NaCl, 0.2% Tween-20, 5% skim milk) and washed five times with T-TBS. The membrane was treated for 2 hours with anti-phosphorylated tyrosine antibodies (1:1000 diluted) as a primary antibody and washed five times with T-TBS before incubation for 1 hour with HRP-conjugated, anti-mouse antibody (1:5000 diluted) as a secondary antibody. After washing with T-TBS, the film was developed with an ECL kit (Amersham, USA) in a dark room.

While the mixture of extracts from *Trachelospermi Caulis* and *Paeonia Suffruticosa* Andrews has low inhibitory activity against IL-6-induced gp130 phosphorylation, as can be seen in FIG. 9, phosphorylated JAK2 was detected at lower levels in the group treated with the extract mixture than in the control and also than in the groups treated with the *Trachelospermi Caulis* extract or the *Paeonia Suffruticosa* Andrews extract. Thus, the extract mixture was observed to inhibit IL-6-induced JAK2 phosphorylation. Consequently, the mixture of extracts from *Trachelospermi Caulis* and *Paeonia Suffruticosa* Andrews according to the present invention has the function of suppressing the release of IL-6.

EXAMPLE 5: Animal Test Using Rheumatoid Arthritis-Induced Mice as Animal Model (CIA)

5-1. Assay of the Mixture of Extracts from *Trachelospermi Caulis* and *Paeonia Suffruticosa* Andrews for Anti-Inhibitory Activity in Arthritis-Induced Mice Bovine type II collagen and adjuvant were separately emulsified, and each emulsion was subcutanesously injected at a dose of 100 μg to the tail. Three weeks later, a booster was achieved by the intraperitoneal injection of 100 μg of bovine type II collagen to induce arthritis. Immediately after the induction, drugs were administered for 21 days and their inhibitory activity against arthritis was measured. The mice were orally administered with suspensions of indomethacin (1 mg/kg), meloxicam (4 mg/kg), bucillamine (300 mg/kg), and the mixture of extracts from *Trachelospermi Caulis* and *Paeonia Suffruticosa* Andrews (SI-000902), every day. For comparison, a normal group (arthritis not induced) and a control (administered with vehicle) were employed. The extract mixture (solid extract, soft extract) was dispersed at a concentration of 20, 50, 100, 200 and 400 mg/kg in a 1% carboxymethyl-cellulose sodium solution before the oral administration. Severity of edema was measured in the four feet of each mouse by blind test with the naked eye every three days and evaluated as grades 0 to 4.

Figure 10:
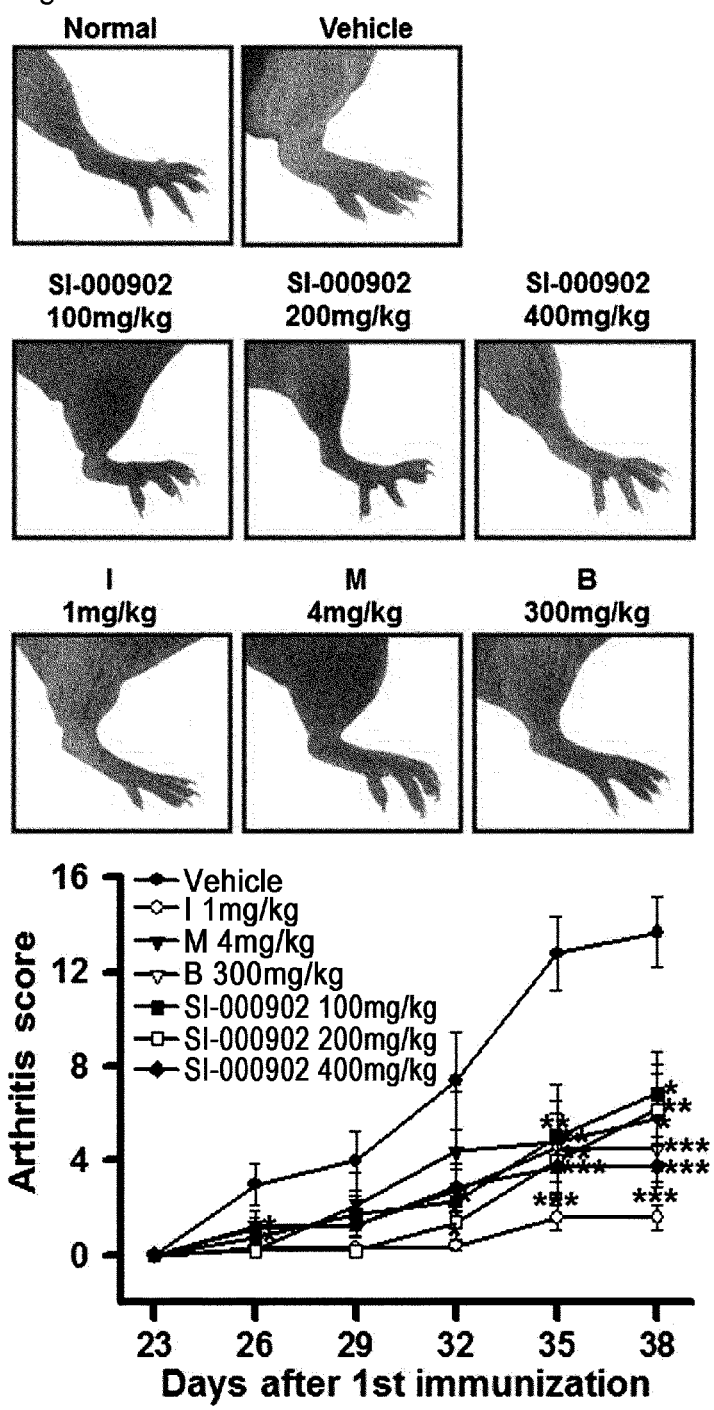
FIG. 10 shows inhibitory effects of a mixture of solid extracts of *Trachelospermi Caulis* and *Paeonia Suffruticosa* Andrews (SI-000902), indomethacin (I), meloxicam (M), and bucillamine (B) on inflammation in photographs and in score curves.

There were no differences in edema between the solid extract (FIG. 10) and the soft extract (FIG. 11) of the extract mixture (SI-000902) according to the present invention. Generally, higher doses of the extract mixture resulted in lower swelling in the feet over the test groups (FIG. 10).

Figure 11:
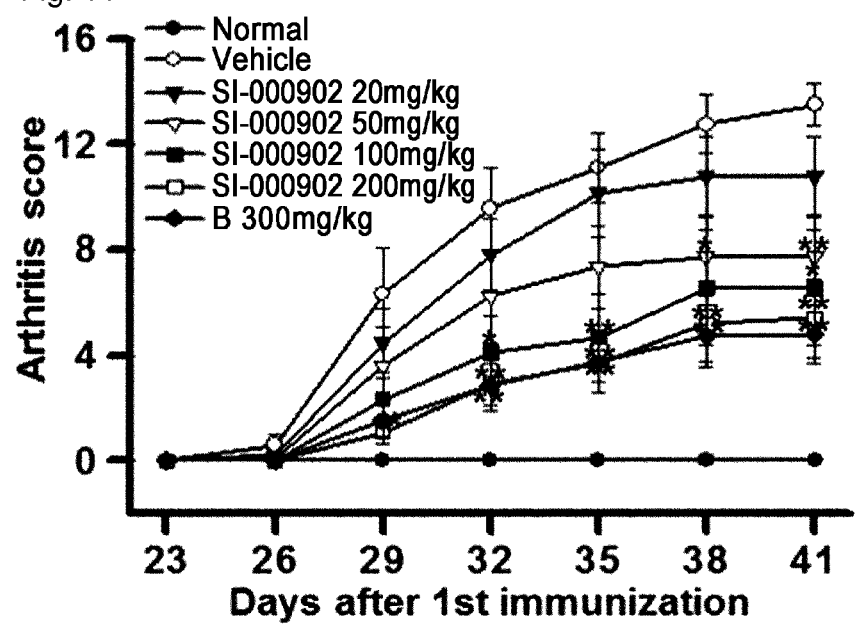
FIG. 11 shows inhibitory effects of a mixture of soft extracts of *Trachelospermi Caulis* and *Paeonia Suffruticosa* Andrews (SI-000902) and bucillamine (B) on inflammation in score curves.

In detail, the solid extract-type mixture was found to have similar inhibitory activity against arthritis to that of the reference drugs indomethacin, meloxicam, and bucillamine as measured in terms of arthritis score. Particularly at a dose of 400 mg/kg, the mixture showed a higher arthritis suppressing effect than did meloxicam and bucillamine (FIG. 10). With reference to arthritis index, the inhibitory effect of the soft extract-type mixture on arthritis was similar to that of bucillamine at a dose of 200 mg/kg (FIG. 11). These results imply that the extract mixture has a similar therapeutic effect on arthritis to that of the conventional medicines for arthritis, and thus can be safely used as natural materials for the suppression and alleviation of arthritis.

5-2. Assay of the Extract Mixture for Suppressive Activity Against Spelenocyte Proliferation in Arthritis-Induced Mice The spleen was aseptically excised from arthritis-induced mice, minced and filtered through a filter to separate and collect only the cells. These cells were treated with RBC lysis buffer to remove red blood cells. The splenocytes thus obtained were plated at a density of $5 \times 10^5$ cells/well into 96-well plates, followed by the addition of 50 μg/ml heat-inactivated type II collagen to each well. The splenocytes were incubated for 72 hours. Six hours before completion of the incubation, the cells were treated with a BrdU labeling solution (5-bromo-2'-deoxyuridine labeling solution) to label DNA. After incubation, the cells were fixed, and suppressive activity against splenocyte proliferation was determined using a BrdU ELISA cell proliferation assay kit (Roche).

Figure 12:
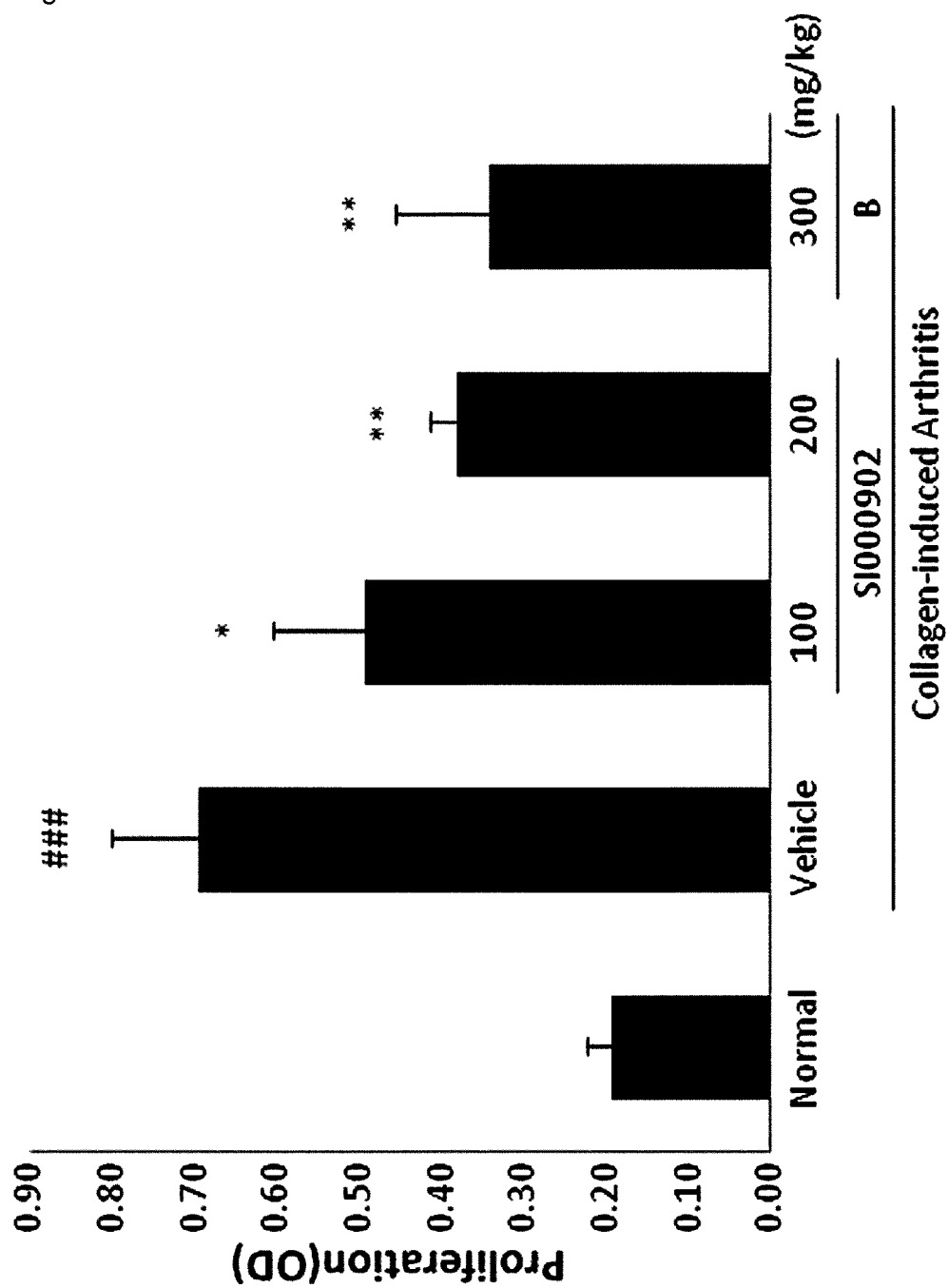
FIG. 12 is a graph showing inhibitory effects of a mixture of soft extracts of *Trachelospermi Caulis* and *Paeonia Suffruticosa* Andrews (SI-000902) and bucillamine (B) on the proliferation of splenocytes of arthritis-induced mice.

Compared to the normal group, the control and the bucillamine-administered group, the proliferation of splenocytes was suppressed in the extract mixture (SI-000902)-administered group. The growth of splenocytes was decreased by 29.2% in the group administered at a dose of 100 mg/kg with the extract mixture and by 45.5% in the group administered at a dose of 200 mg/kg. This suppressive activity was comparable to that of the positive control bucillamine (51.1% inhibition) (FIG. 12). Therefore, the extract mixture (SI-000902) according to the present invention can be used for regulating immune responses as it was observed to suppress the proliferation of splenocytes, which play an important role in immune responses.

5-3. Assay of the Extract Mixture for Inhibitory Activity Against IFN-γ and IL-2 of Splenocytes in Arthritis-Induced Mice The spleen was aseptically excised from arthritis-induced mice and used to give a cell suspension. This suspension was treated with RBC lysis buffer to remove red blood cells. The splenocytes thus obtained were plated at a density of 5×10$^6$ cells/well into 24-well plates, followed by the stimulation of the cells with 50 μg/ml heat-inactivated type II collagen per well. The splenocytes were incubated for 48 hours. The level of the cytokines IFN-γ and IL-2 in the medium was measured using an ELISA kit (R&D systems) to examine the inhibitory effect of the extract mixture on the cytokines.

Compared to the normal group, the control and the bucillamine-administered group, the activity of IFN-γ and IL-2 was suppressed in the extract mixture (SI-000902)-administered group. The activity of IFN-γ was decreased by 60.6% in the group administered at a dose of 100 mg/kg with the extract mixture and by 74.7% in the group administered at a dose of 200 mg/kg. As for IL-2, its activity was decreased by 25.3% upon administration of the extract mixture at a dose of 100 mg/kg, and by 36.8% at a dose of 200 mg/kg. This suppressive activity was comparable to that of the positive control bucillamine (88.5% (IFN-γ), 39.1% (IL-2)). Therefore, the extract mixture (SI-000902) according to the present invention can be used for regulating immune responses (FIG. 13).

EXAMPLE 6: Test for Morphological Stability of Dry Mixed Granules Based on Extracts from *Trachelospermi Caulis* and *Paeonia Suffruticosa* Andrews 6-1. Morphological Stability of Dry Granules Based on Extracts from *Trachelospermi Caulis* and *Paeonia Suffruticosa* Andrews As described in Preparation Example 4, the respective soft extracts from *Trachelospermi Caulis* and *Paeonia Suffruticosa* Andrews were dried at reduced pressure and pulverized into granules the morphological stability of which was monitored at room temperature.

With the lapse of time, moisture absorption caused the dry granules of *Trachelospermi Caulis* to melt. Also, the dry granules of *Paeonia Suffruticosa* Andrews melted due to their hygroscopicity. Although their melting time varied depending on relative humidity, both the dry granules of *Trachelospermi Caulis* and *Paeonia Suffruticosa* Andrews went morphologically back to the initial soft extracts within one to two weeks.

In addition, an examination was made to see whether dried materials of *Trachelospermi Caulis* and *Paeonia Suffruticosa* Andrews could be formulated into a solid form without melting when using a typical method. In this regard, immediately after being dried, *Trachelospermi Caulis* and *Paeonia Suffruticosa* Andrews materials were admixed with an excipient and subjected to a tabletting process. For the first several minutes, tablets were formed, but while 10 minutes had lapsed since the formation, the tablets collapsed due to their own hygroscopicity. In spite of a trial for processing into products before the disappearance of the morphology, the materials of *Trachelospermi Caulis* and *Paeonia Suffruticosa* Andrews absorbed too fast to guarantee sufficient processing time.

6-2. Morphological Stability of Microcrystalline Cellulose-Containing Dry Mixed Granules Based on *Trachelospermi Caulis* and *Paeonia Suffruticosa* Andrews As described in Preparation Example 5, the respective soft extracts from *Trachelospermi Caulis* and *Paeonia Suffruticosa* Andrews were mixed at different weight ratios with microcrystalline cellulose to prepare dry mixed granules of *Trachelospermi Caulis* and dry mixed granules of *Paeonia Suffruticosa* Andrews, both containing microcrystalline cellulose. In this context, first, 1 weight part of each of the soft extracts from *Trachelospermi Caulis* and *Paeonia Suffruticosa* Andrews was mixed with 0.5 weight parts of microcrystalline cellulose. Separately, 1 weight part of each of the soft extracts from *Trachelospermi Caulis* and *Paeonia Suffruticosa* Andrews was mixed with 2 weight parts of microcrystalline cellulose (dry mixed granules 1 and 2 of Preparation Example 5, respectively).

The dry mixed granules containing 0.5 weight parts of crystalline cellulose melted into a soft form with time, and thus could not guarantee sufficient time to a tabletting process.

The *Trachelospermi Caulis*-based dry mixed granules containing 2 weight parts of crystalline were observed to maintain their granular morphology. This morphological maintenance was also found in the *Paeonia Suffruticosa* Andrews-based dry mixed granules. Although partially aggregating with time, these granules could guarantee a period of time sufficient to perform a tabletting process.

6-3. Morphological Stability of Silicon Dioxide-Containing D Mixed Granules Based on *Trachelospermi Caulis* and *Paeonia Suffruticosa* Andrews As described in Preparation Example 6, the respective soft extracts from *Trachelospermi Caulis* and *Paeonia Suffruticosa* Andrews were processed into silicon dioxide-containing dry mixed granules based on *Trachelospermi Caulis* and *Paeonia Suffruticosa* Andrews.

The *Trachelospermi Caulis*-based dry mixed granules were observed to maintain their morphology even with the lapse of three months. This morphological maintenance was also found in the *Paeonia Suffruticosa* Andrews-based dry mixed granules. Further, these dry mixed granules based on *Trachelospermi Caulis* and *Paeonia Suffruticosa* Andrews were resistant to moisture, so that they could be tabletted for a long period of time without collapsing or curing.

6-4. Long-Term Stability of Tablets Formed of Silicon Dioxide-Containing Dry Mixed Granules Based on *Trachelospermi Caulis* and *Paeonia Suffruticosa* Andrews In the case where tablets are made of highly hygroscopic materials, the stability of the tablets have many problems: the tablets are apt to collapse; the materials partially melt or aggregate and then becomes hard so that disintegration is delayed. Tablets were made of the silicon dioxide-containing dry mixed granules based on *Trachelospermi Caulis* and *Paeonia Suffruticosa* Andrews, prepared in Preparation Example 6. The tablets were observed to maintain their morphology after they were exposed at room temperature for a long period of time.

Also, the tablets neither collapsed nor became hard, but guaranteed constant time of disintegration even after storage at high temperature in a highly moist environment (Temp.: 40° C., RH:75%), as shown in Table 5.

TABLE 5

| Storage Time of Tablet | Time of Disintegration |
| --- | --- |
| Just after preparation (0 month) | 16 min |
| 1 month after preparation | 17 min |
| 6 month after preparation | 16 min |

Also, contents of the index substances were stably maintained with time, as shown in Table 6, below.

TABLE 6

|  | Paeonia Suffruticosa Andrews Paeoniflorin(%) | Trachelospermi Caulis Arctigenin(%) |
| --- | --- | --- |
| Initial (2010 Oct. 8) | 2.87 | 0.22 |
| 2 months (2010 Dec. 3) | 2.81 | 0.24 |
| 3 months (2011 Jan. 19) | 2.85 | 0.25 |
| 4 months (2011 Feb. 28) | 2.81 | 0.26 |
| 6 months (2011 Apr. 10) | 3.06 | 0.24 |
| 7 months (2011 May 19) | 3.12 | 0.25 |

6-5. Morphological Stability of Corn Starch-Containing Dry Mixed Granules Based on *Trachelospermi Caulis* and *Paeonia Suffruticosa* Andrews The respective corn starch-containing dry mixed granules based on *Trachelospermi Caulis* and *Paeonia Suffruticosa* Andrews, prepared in Preparation Example 7, were observed to be less affected by moisture than was the granules prepared in Preparation Example, as measured for morphological stability, but eventually melted into soft form.

When formulated in mixture with an excipient into tablets, both the *Trachelospermi Caulis* and the *Paeonia Suffruticosa* Andrews-based dry mixed granules collapsed, like the dry granules prepared in Preparation Example 4. Thus, the corn starch-containing dry mixed granules based on *Trachelospermi Caulis* or *Paeonia Suffruticosa* Andrews are not suitable for the production of products under a GMP facility.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for treating an inflammatory disease, comprising administering an effective amount of a solid oral pharmaceutical formulation to a subject in need thereof, wherein the formulation consists essentially of:
   (a) silicon dioxide, and
   (b) a mixture of ethanolic extracts of *Trachelospermi Caulis* and *Paeonia Suffruticosa* Andrews in a ratio of 1:1 to 3:1 as an active agent,
   wherein the *Trachelospermi Caulis* extract comprises 0.05 to 1.5 wt % arctigenin, and
   wherein the *Paeonia Suffruticosa* Andrews extract comprises 1.8 to 5.3 wt % paeoniflorin.

2. The method of claim 1, wherein the formulation suppresses release of nitric oxide (NO), IL-6 or IL-1β.

3. The method of claim 1, wherein the inflammatory disease is selected from the group consisting of edema, dermatitis, allergy, atopy, asthma, conjunctivitis, peridontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, systemic lupus erythematosus, fibromyalgia, psoriatic arthritis, osteoarthritis, rheumatoid arthritis, periarthritis of shoulder, tendonitis, tenosynovitis, myositis, hepatitis, cystitis, nephritis, sjogren's syndrome and multiple sclerosis.

4. The method of claim 3, wherein the inflammatory disease is rheumatoid arthritis.

5. The method of claim 1, wherein the formulation further comprises a pharmaceutically acceptable excipient for oral administration.

6. The method of claim 5, wherein the excipient is microcrystalline cellulose or potassium silicate.

7. The method of claim 5, wherein the formulation is in a form selected from the group consisting of a powder, a granule, a hard capsule and a tablet.

8. The method of claim 1, wherein the ratio of (a) silicon dioxide to (b) the mixture of extracts is from 1:3 to 1:1.

* * * * *